(12) United States Patent
Hansen et al.

(10) Patent No.: US 11,235,330 B2
(45) Date of Patent: Feb. 1, 2022

(54) HYDROGEL MEMBRANE AND METHODS FOR SELECTIVE RETRIEVAL OF MICROBIAL TARGETS

(71) Applicant: Kansas State University Research Foundation, Manhattan, KS (US)

(72) Inventors: Ryan R. Hansen, Manhattan, KS (US); Thomas G. Platt, Manhattan, KS (US); Andre Jacobus van der Vlies, Manhattan, KS (US)

(73) Assignee: Kansas State University Research Foundation, Manhattan, KS (US)

( * ) Notice: Subject to any disclaimer, the term of this patent is extended or adjusted under 35 U.S.C. 154(b) by 128 days.

(21) Appl. No.: 16/753,598

(22) PCT Filed: Oct. 5, 2018

(86) PCT No.: PCT/US2018/054663
§ 371 (c)(1),
(2) Date: Apr. 3, 2020

(87) PCT Pub. No.: WO2019/071163
PCT Pub. Date: Apr. 11, 2019

(65) Prior Publication Data
US 2020/0330984 A1    Oct. 22, 2020

Related U.S. Application Data

(60) Provisional application No. 62/568,984, filed on Oct. 6, 2017.

(51) Int. Cl.
*B01L 3/00* (2006.01)
*B01D 63/08* (2006.01)
(Continued)

(52) U.S. Cl.
CPC ........ *B01L 3/50853* (2013.01); *B01D 63/088* (2013.01); *B01D 67/0006* (2013.01);
(Continued)

(58) Field of Classification Search
CPC ........... B01L 3/50853; B01L 2300/069; B01L 2300/044; B01L 2300/0819;
(Continued)

(56) References Cited

U.S. PATENT DOCUMENTS

| | | |
|---|---|---|
| 2003/0175824 A1 | 9/2003 | Pishko et al. |
| 2011/0111033 A1 | 5/2011 | Stover et al. |

(Continued)

FOREIGN PATENT DOCUMENTS

WO    2017087693    5/2017

OTHER PUBLICATIONS

Kloxin, et al., "Photodegradable Hydrogels for Dynamic Tuning of Physical and Chemical Properties", Science, 2009, vol. 324, issue 5923, pp. 59-63 (abstract attached).

Hansen, et al., "Stochastic Assembly of Bacteria in Microwell Arrays Reveals the Importance of Confinement in Community Development", PLoS ONE, 2016, vol. 11, issue 5 (18 pages).

(Continued)

*Primary Examiner* — Michael L Hobbs
(74) *Attorney, Agent, or Firm* — Hovey Williams LLP

(57) ABSTRACT

Polymer hydrogels and methods for selective retrieval of microbial targets from microwells and other cell culture devices. The methods use semi-permeable, photodegradable hydrogel membranes that permit exchange of nutrients and waste products but seals motile bacteria and other microbes within microwells. Light exposure can be used to degrade the hydrogel membrane in a targeted manner and release the microbes from targeted microwells for further study.

20 Claims, 14 Drawing Sheets

(51) Int. Cl.
  *C12M 1/32* (2006.01)
  *B01D 67/00* (2006.01)
  *B01D 71/52* (2006.01)
  *C12M 1/00* (2006.01)
  *C12M 1/12* (2006.01)

(52) U.S. Cl.
  CPC ............ *B01D 71/52* (2013.01); *C12M 23/12* (2013.01); *C12M 23/20* (2013.01); *C12M 37/04* (2013.01); *B01D 2323/30* (2013.01); *B01D 2323/36* (2013.01); *B01D 2325/36* (2013.01); *B01D 2325/44* (2013.01); *B01L 2300/044* (2013.01); *B01L 2300/0819* (2013.01)

(58) Field of Classification Search
  CPC ............ B01D 63/088; B01D 67/0006; B01D 2323/30; B01D 2323/36; B01D 2325/36; B01D 2325/44; B01D 2325/028; B01D 69/02; C12M 23/12; C12M 23/20; C12M 37/04; G01N 2001/2886
  See application file for complete search history.

(56) References Cited

U.S. PATENT DOCUMENTS

| | | |
|---|---|---|
| 2014/0271843 A1 | 9/2014 | Ma et al. |
| 2016/0023834 A1 | 1/2016 | DiLiberto |
| 2020/0292944 A1* | 9/2020 | Sofman .................. G03F 7/343 |

OTHER PUBLICATIONS

Halsted, et al., "Development of Transparent Microwell Arrays for Optical Monitoring and Dissection of Microbial Communities" J of Vacuum Science & Technology B, 2016, vol. 34, issue 6 (abstract attached).

Tibitt, et al., "Mechanical Properties and Degradation of Chain and Step-Polymerized Photodegradable Hydrogels", Macromolecules, 2013, vol. 46, issue 7, pp. 2785-2792.

Kharkar, et al., "Designing Degradable Hydrogels for Orthogonal Control of Cell Microenvironments", Chem. Soc. Rev., 2013, vol. 42, issue 17, pp. 7335-7372.

International Search Report and Written Opinion in corresponding PCT/US2018/054663, dated Dec. 10, 2018.

Timm, et al., "Assembly and Tracking of Microbial Community Development Within a Microwell Array Platform", J Vis Exp. Jun. 6, 2017;(124):55701.

* cited by examiner (A) Pre-fabricated microwell substrate (B) Cell seeding

- glass substrate
- SU-8 wells
- parylene mask
- PEG-based membrane attachment
- growth media (C) Mask removal (D) Membrane attachment (E) Culture / growth monitoring Microscope objective

HYDROGEL MEMBRANE AND METHODS FOR SELECTIVE RETRIEVAL OF MICROBIAL TARGETS

CROSS-REFERENCE TO RELATED APPLICATIONS

The present application is the U.S. National Stage of International Patent Application No. PCT/US2018/054663, filed Oct. 5, 2018, which claims the priority benefit of U.S. Provisional Patent Application Ser. No. 62/568,984, filed Oct. 6, 2017, entitled MICROWELL ARRAY PLATFORM FOR HIGH-THROUGHPUT SCREENING AND DISCOVERY OF MICROBIAL INTERACTIONS, each of which is incorporated by reference in its entirety herein.

FEDERALLY SPONSORED RESEARCH OR DEVELOPMENT

This invention was made with government support under contract no. MCB-1650187 awarded by the National Science Foundation. The government has certain rights in the invention.

BACKGROUND OF THE INVENTION

Field of the Invention

The present invention relates to photosensitive hydrogel membranes for selective retrieval of microbial targets.

Description of Related Art

Plant and animal microbiomes play an important role in shaping host health and physiology. The dynamics of these highly diverse communities depend on a range of factors, including host traits, environmental conditions, and interactions among microbes. Understanding the complex interplay of these factors will help unravel the consequences of microbiomes on host health and ecosystem functions as well as aid efforts to engineer microbiomes toward desired outcomes. Microbial interactions are often context dependent, influenced by the physical and chemical characteristics of the environment as well as species abundance. Consequently, many microbial interactions are poorly characterized or unknown because traditional methods probe these interactions using low-throughput co-culturing approaches that measure growth of bulk cell populations in homogenous liquid environments or over solid media.

New tools driven by micro- and nanotechnology are expected to become common-place in the microbiology laboratory, as they allow for precise cellular measurements at the appropriate scale. These instruments will ultimately enable the microbiologist to piece together the complex processes that drive the structure and function of microbiomes in their natural ecosystems. In recent years, several microfluidic approaches have been developed for studying bacterial growth and behavior in precisely controlled physicochemical environments. This enables manipulation of bacteria at the single cell level and has uncovered new insights into microbial synergy and mutualism, quorum sensing-mediated behaviors, as well as new insight into the role that spatial habitat structure plays in driving new community phenotypes. A number of microwell formats have also been introduced to offer the benefits of high-throughput, single cell analysis. Despite recent advances, critical limitations still exist for applications addressing the diverse and complex interactions occurring in a microbial community. For one, most platforms designed to probe inter-cellular interactions are not well suited to explore the vast number of interactions occurring within microbiomes. Secondly, many platforms are operationally complex, limiting the translational capacity and commercial potential. Further, retrieval of cells from microwell arrays with high spatial precision remains a major technical hurdle that prevents follow-up genetic and phenotypic characterization of cells within observed microwells.

The utility of microwell arrays, particularly in screening applications, could be significantly expanded if cells of interest could be removed from individual wells for subsequent genetic and phenotypic characterizations. In particular, coupling of 'Omic' technologies (e.g. 16S rRNA sequencing, whole genome sequencing, RNA-seq, etc.) with microwell array measurements could be enabled if selective extraction of cells from wells and in some cases subsequent enrichment through culture is achieved. For example, microwells could be used to examine a large number of mutant genotypes for a target phenotype during a mutant library screen, but would require subsequent isolation of selected mutants from individual wells for mutation mapping.

SUMMARY OF THE INVENTION

The present invention is broadly concerned with a new cell retrieval approach using semi-permeable, photodegradable membranes that permit exchange of nutrients and waste products and seals motile bacteria and other microbes within microwells. The photo-degradability of the membrane enables individual wells of interest to be opened using patterned UV light for selective release and retrieval. Extraction can occur in parallel from any number and combination of wells defined by the user. These advancements represent a new use for light-responsive hydrogels and the ability to retrieve cells from microwells with high spatial precision enables several applications that require the isolation and characterization of cells with rare phenotypes from heterogeneous populations.

Thus, methods and materials described herein concern selective retrieval of microbial targets from cell culture. The technique generally comprises culturing a plurality of microbes in a cell culture device. Exemplary devices comprising a substrate having a top surface and a plurality of microwells (or microchannels) formed therein, wherein each microwell is defined by a respective opening in the top surface, a bottom surface spaced from the top surface, and an interior sidewall extending between the opening and bottom surface. Depending upon the procedure, one or more of the microwells will include one or more microbes distributed therein. A crosslinked hydrogel membrane is then formed over the top surface, wherein said membrane seals the respective opening of one or more of the microwells such that the microbes are confined to their respective microwells. Once microbial targets have been identified in microwells of interest, the crosslinked hydrogel membrane is exposed to a pattern of UV light to yield exposed and unexposed areas of the crosslinked hydrogel membrane. Advantageously, the exposed areas are degraded over one or more microwells of interest such that the seal over these particular microwells is broken to yield unsealed microwells; however, unexposed areas over one or more additional microwells remain sealed. Therefore, one can then selectively retrieve microbial targets from the particular one or more unsealed microwells for further study.

The proof of concept studies use a light-responsive poly(ethylene glycol) (PEG) hydrogel as a photodegradable membrane and silicon microarrays seeded with the model bacterium *Agrobacterium tumefaciens*, the causative agent of crown gall disease in a wide range of plants including apples, walnuts, and sunflowers. As is common among bacteria, the success of this plant pathogen is heavily influenced by interactions with other bacteria, many of which are unknown. The platform allows tracking or end-point observation of cell growth based on fluorescence intensity measurement of mCherry-expressing *A. tumefaciens* inside of microwells. Using a light patterning tool, selected microwells can be opened individually or in parallel, thereby allowing subsequent retrieval of viable cells. This material-based approach affords a high degree spatial control over bacteria retrieval and can be adapted to other high-throughput screening formats. For these reasons, we expect that this approach will be a powerful tool for microbiome engineering efforts, as well as other applications where screening and studying cell-cell interactions is important.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

The present invention is concerned with hydrogel membranes and methods for confinement and selective retrieval of microbes from cell culture devices, such as culture dishes and plates, microwell plates, or microfluidics devices. Embodiments of the invention relate to photosensitive hydrogel membranes that can be used to cover openings in these devices to trap microbes therein, such as bacteria, fungi, viruses, and microbial parasites. The membrane can be selectively removed, such as over individual microwells containing a target microbe (e.g., single microbial strain) or microbe community of interest (e.g., heterogenous microbial mixture), for retrieval of the target from only those uncovered areas. This allows further cell culture, analysis, or other processes for further study, including identification of microbial interactions occurring within that target community. The source of microbes that compose the heterogeneous communities applied can be varied depending on the application. For example, to identify environmental microbes that influence the function of a focal microbe the heterogeneous community may be composed of that focal microbe stochastically combined with a variety of different subsets of microbes obtained from a more complex environmental microbiome (e.g., soil samples, gut/tissue samples, etc.). This platform also allows high-throughput screening of mutant libraries to identify genetic factors associated with observable phenotypes, including those depending on interactions with other microbes. The ability to remove microbial cells of interest from a microwell array at high resolution (e.g., extraction from 1-2 um diameter wells) is a novel capability that is unachievable with current state of the art, and will enable sequencing and identification of strains and mutant genotypes that effect the function of a focal species.

Figure 1:
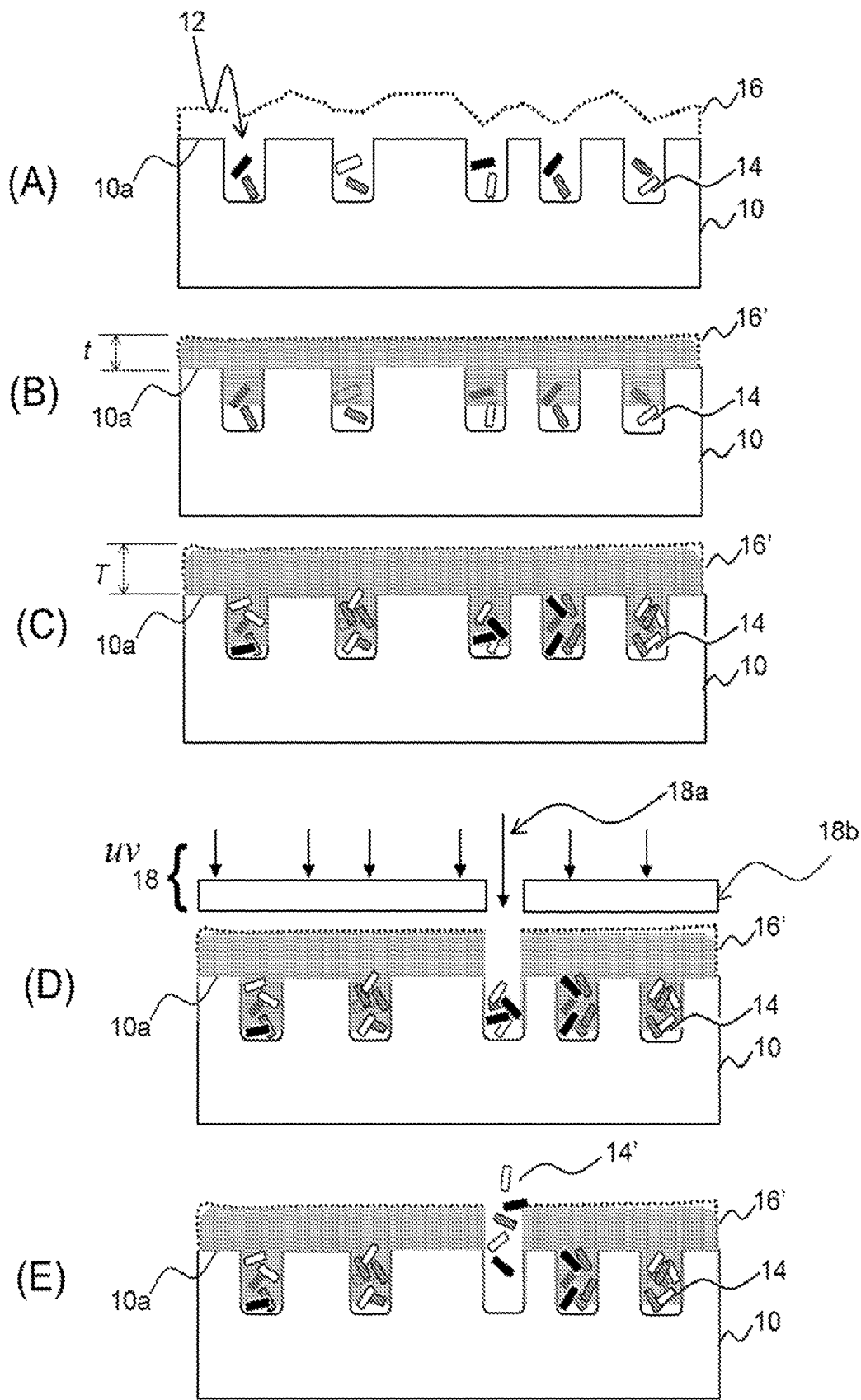
FIG. 1(A)-(E) shows schematic drawings depicting a cross-sectional view of processing of a substrate (not to scale) using the photosensitive hydrogel membranes according to an embodiment of the invention.

FIGS. 1(A)-(E) illustrate an exemplary embodiment of the approach. In more detail, referring to FIG. 1(A), a substrate 10 having a surface 10a is provided. FIG. 1(A) depicts a cross-sectional illustration of a microwell plate including a plurality of microwells 12 formed in the substrate surface 10a. The substrate 10 could also be a microfluidics-type device comprising one or more microchannels or passageways for cells and liquid to move across the device without departing from the scope of the invention. In general, cell culture substrates 10 have a substantially planar top surface 10a and a plurality of wells or channels 12 disposed across and formed within the top surface 10a. It will be appreciated that the arrangement of wells 12 in a microwell array may be varied. In other words, the spacing between adjacent wells 12 may be uniform or non-uniform across the substrate surface 10a. The inventive approach is particularly suitable for high density arrays. A variety of microwell plates and/or microfluidics devices are commercially available and suitable for use with the inventive approach. Substrates 10 may also be custom fabricated for use in the inventive platform. Microwell plates are commonly available in 6, 12, 24, 48, 96, 384 or 1536-well configurations, typically arranged in a rectangular matrix; however, microwell arrays can be designed to contain up to $10^5$ to $10^6$ microwells in a single array.

Each well or channel 12 is defined by an opening in the top surface 10a, a bottom surface spaced from the opening, and an interior sidewall surface extending between the bottom surface and the opening. In other words, the microwells 12 do not extend all the well through the substrate 10. One or more microwells 12 may be laterally interconnected by microchannels (not shown) without departing from the scope of the invention. The interior sidewall surface may be substantially perpendicular to the top surface 10a, or may be angled as desired. The individual microwells or channels 12 in the substrate 10 may be of a uniform size (depth and/or diameter) or may vary across the substrate as desired. For example, wells can be designed with varying diameters across the substrate. Exemplary microwell 12 openings will have a depth as measured from the top surface 10a to the bottom surface of between 5 μm and 100 μm, and a diameter of 1 μm and 150 μm (where "diameter" also refers to the largest lateral dimension of the opening in a square microwell). Exemplary microchannels will have a depth as measured from the top surface 10a to the bottom surface of between 5 μm and 100 μm, a width of 1 μm and 150 μm, and a variable length (where the "width" refers to the dimension between opposing sidewalls defining the channel). Further, the rim of the microwell or channel openings may be flush with the top surface 10a of the substrate, as depicted. Microwell plates are also available with recessed openings relative to the top surface of the substrate 10a (not shown).

In one or more embodiments, the substrate 10 may be transparent. In one or more embodiments, the substrate 10 may by opaque. Regardless, the substrate 10 can be made of any biocompatible material suitable for culturing microbial cells. For example, the biocompatible material could be a biocompatible polymer, including without limitation, polystyrene, polypropylene, polycarbonate, polyolefin, polymethyl methacrylate, polydimethylsiloxane, silicone rubber, polyethylene, acrylic, polyester, ethylene vinyl acetate, polysulfone, polytetrafluoroethylene, copolymers thereof, and/or composites thereof. Microwell and microfluidics substrates can also be made of glass, quartz, silicon dioxide, and silicon wafer (crystalline silicon) and the like. Microwell and microfluidics substrates may also be comprised of combinations of these materials, such as in the case of microwell arrays or microfluidics channels having glass bottoms, but sidewalls of patterned PDMS or other material formed on top of the glass bottom.

As depicted in FIG. 1(A), a plurality of microbial cells 14 are seeded onto the substrate 10 where one or more cells 14 is dispersed into each well 12, along with suitable cell culture media components in the wells 12. In one or more embodiments, the wells or channels 12 can be sized and arrayed to limit the number of cells 14 in each well, for example, to facilitate stochastically pairing two microbes for study.

As depicted in FIG. 1(A), a hydrogel precursor solution 16 is then applied across the substrate surface 10a, for example by spincoating, spraying, dripping, pooling, puddling, etc. the precursor solution 16 onto the substrate surface 10a. The hydrogel precursor solution 16 may also first be applied to a second planar substrate (e.g., glass slide), which is then inverted and applied in an opposing face-to-face engagement with the substrate surface 10a to bring the hydrogel precursor solution 16 into contact with the substrate surface 10a. In one or more embodiments, one or more spacers may be included on either substrate to maintain a predefined spacing between the respective surfaces of the substrates when they are brought into contact. In this embodiment, the second substrate helps press and "flatten" the hydrogel precursor solution 16 as hydrogelation occurs. It also helps control the thickness of the hydrogel layer. It will be appreciated that one or more intermediate layers (not shown) could also first be formed on the top surface (10a), with the hydrogel precursor solution 16 being applied to the uppermost intermediate layer. Suitable hydrogel precursor solutions 16 for use in forming the hydrogel membrane 16' include any biocompatible photosensitive compositions that can be selectively patterned and decrosslinked upon exposure to light. Thus, such hydrogel precursors will generally include crosslinkable hydrophilic polymers wherein at least one polymer has a photolabile protecting group. Preferably, at least one polymer is a multi-functional polymer (e.g., difunctional, trifunctional, or tetrafunctional) to facilitating the crosslinked network and may be considered the "crosslinking agent."

Various biocompatible hydrogel systems have been developed and can be used in the invention, and/or modified to include a photolabile protecting group. Hydrogel polymers are selected to be non-toxic to cells, and hydrophilic to permit transport of nutrients and waste products to support bacterial cell growth within microwells while inhibiting microbial transport. Polymer systems are also preferably selected to generate hydrogel networks with uniform crosslinking density and microstructure (e.g., mesh size in the nanometer range), allowing for uniform diffusion across the array. In one or more embodiments, the hydrogel precursor solution is based upon a thiol-acrylate Michael-type addition polymerization reaction. Exemplary polymers of this type include poly(ethylene glycol)s, which can be respectively functionalized with acrylate, methacrylate, allyl ether, maleimide, vinyl sulfone, ester, vinyl ether, or thiol groups for crosslinking, and modified to include photolabile protecting groups. In one or more embodiments, the hydrogel precursor solution comprises a mixture of PEG-based acrylate monomers and multi-functional (preferably tetrafunctional) PEG thiols dispersed in an aqueous solvent system, along with at least one photolabile protecting group that is incorporated into the hydrogel backbone. Thus, in one or more embodiments, the crosslinked hydrogel is formed by step-growth polymerization of a photodegradable polyethylene glycol (PEG) diacrylate monomer with a PEG tetrathiol crosslinker dispersed in PBS. Preferably PEG diacrylates are used, which are further modified with photolabile nitrobenzyl groups causing the polymer matrix to degrade upon UV exposure. Such photolabile protective groups are cleaved upon exposure to light of the appropriate wavelength. Other suitable polymer/monomer systems for hydrogel formation that can be modified with a photocleavable protective group include polyhydroxyethylmethacrylate, poly-l-lysine, polydopamine, collagen, cellulose, gelatin, chitosan, hyaluronic acid, heparin, agarose, alginate, agar, and combinations thereof. Hydrogels that contain components found in bacteria exopolysaccharides (for example, polysaccharides that contain n-acetyl glucosamine or other common extracellular glycans) could also be used for hydrogel formation.

Examples of additional suitable photolabile groups that can be used to render such polymer/monomer systems photosensitive include aromatic moieties, such as nitrophenethyl compounds and derivatives thereof including photocleavable peptides (3-amino-3-(2-nitrophenyl)-propionate amino acid in the peptide chain) and dimethoxy derivatives (nitroveratryl), o-nitrobenzyloxycarbonyl, carbonyl-based protecting groups, benzyl-based protecting group (e.g., carboxybenzyls), coumarin derivatives, p-methoxyphenacyl groups and derivatives, 3-nitro-2-naphthalenemethanol, and the like. In general, suitable protecting groups will have an aromatic moiety for absorbance in the desired wavelength, and remain biocompatible upon cleavage. Type I photoinitiators (also known as Norish type I initiators) could also be possibly used in they hydrogel. These molecules contain benzoyl groups that cleave after absorbing UV light to produce two fragmented molecules containing free radicals. The presence of free radicals may be undesirable for certain applications involving bacteria.

As depicted in FIG. 1(B), the hydrogel precursor solution 16 preferably distributes across the surface 10a and preferably flows (or is pushed by the second substrate, not shown) into the individual microwells 12 before complete crosslinking and gelation occurs to yield the crosslinked hydrogel membrane 16' having an initial thickness t. Again, as noted above, spacers can be used to help control this initial thickness t when a second substrate is used to "sandwich" the hydrogel between the two substrates. In one or more embodiments, the initial thickness t is preferably from about 10 μm to about 50 μm, although thicker or thinner layers could be used. Thus, the resulting membrane 16' comprises (consists essentially, or consists of) a crosslinked polymer that degrades under light. Advantageously, upon contacting the cell culture media inside the wells 12, the polymer network making up the crosslinked hydrogel membrane 16' will swell to an increased thickness T, as depicted in FIG. 1(C). This increased thickness T may be up to about 150 μm, depending up on the initial thickness used and the particularly hydrogel matrix formed. It will be appreciated that thinner membranes are particularly desired, so long as they act as an adequate barrier to inhibit microbe migration (chemotaxis) from the wells 12.

The crosslinked hydrogel membrane 16' also swells further into the microwells 12 essentially "locking" the membrane in place, and sealing off the respective opening of each microwell 12. This provides the added benefit of preventing motile bacteria or other microbes from escaping from the wells 12 during cell culture and study. Depending upon the substrate used, physical attachment of the membrane to the microwell array may also be facilitated by scalloped sidewalls of the microwells resulting from the Bosch etching process on etched microwells. Surface treatments may also be used on the substrate surface 10a to enhance adhesion of the membrane and prevent delamination to inhibit cell migration outside of the wells.

Thus, the crosslinked hydrogel membrane 16' as depicted in FIG. 1(C) forms a physical barrier that prevents microbes from moving out of the microwells 12 but allows diffusion of nutrients, oxygen, and metabolic waste products across the membrane 16' to facilitate culturing of the cells 14. It has been shown that the membrane 16' can also be (slowly) locally degraded by the microbes 14 to generate space for growth within the wells 12, if needed.

It will be appreciated that alternative approaches for sealing the wells with a crosslinked hydrogel membrane are also contemplated herein. In one or more embodiments, instead of the crosslinked hydrogel membrane polymerizing/crosslinking in situ on the substrate as described above, the crosslinked hydrogel membrane could be pre-formed and then applied as a layer, film, or strip over the top of the substrate after seeding the cells. That is, the hydrogel precursor solution could be cast onto a separate planar substrate and crosslinked to form a crosslinked hydrogel layer or film that could then be peeled away and applied to the substrate 10 over the top of the wells 12. Further, it is contemplated that in an alternative in situ hydrogelation approach, the substrate surface 10a could be treated or functionalized to contain one or more components of the hydrogel system, such as a suitable crosslinking agent and/or catalyst to react with the hydrogel precursor solution 16 when it is applied to the substrate 10. In this manner, the hydrogel precursor solution 16 will not react or begin to polymerize or crosslink until it contacts the functionalized surface 10a of the substrate 10.

Regardless of the embodiment, once the wells 12 are sealed with the hydrogel membrane 16', the microbial cells 14 can be cultured and monitored under the desired conditions for the desired period of time. Thus, in preferred embodiments, the resulting hydrogel membrane 16' is preferably at least translucent, and more preferably substantially transparent (e.g., at least 60%, 70%, or 80%, and preferably at least 90% light transmittance) so that the microbial cells entrapped under the membrane 16' can be visually monitored through the membrane 16'. The microbial cells entrapped under the membrane 16' can also be monitored through the substrate 10, for example, from underneath using an inverted microscope and/or by flipping the substrate over to view the microbial cells through the substrate 10. In one or more embodiments, the crosslinked hydrogel membrane 16' can be covered/coated and/or the entire plate can be immersed in cell culture media. This helps the membrane 16' to swell and further "lock" into place. It also keeps the membrane 16' from drying out and facilitates exchange of nutrients/waste across the membrane 16'. The sealed substrate 10 can be monitored and analyzed while remaining in the cell culture media and/or can be removed periodically for monitoring and analysis.

In one or more embodiments, the platform can be used to study microbe-microbe interactions. In one embodiment, the method is used to stochastically pair a focal species expressing a detectable (e.g., fluorescent) marker together with single cells from an environmental microbiome in thousands of compositionally unique microwell communities present in a high-density microarray format. Pairs are trapped within respective wells using the membrane and monitored for focal species phenotypes using fluorescent microscopy. This approach is particularly relevant for studying soil microbiomes. Thousands of microbes persistently live on plant roots where microbial interactions help shape these communities and are a critical factor in determining plant health. Traditional approaches test only a few interactions at a time, leaving many microbial communities poorly characterized. By simultaneously testing thousands of different microbial interactions, this approach will greatly accelerate the pace of discovery. The platform can also be used for high-throughput screening of mutant libraries to identify genetic factors affecting phenotypes that can be observed in microwells, including those associated with microbial interactions. To identify genetic factors influencing interactions between the focal species and other microbes, mutant libraries can be seeded into wells together with either a specific microbe or a pool of environmental isolates. Regardless, the cells are trapped within their respective wells using the hydrogel membrane and then monitored in parallel, for example with a fluorescent microscope, for effects on the focal species. The platform can generate high-density, compositionally unique, independent co-culture sites (wells) that allow for simultaneous monitoring of many interactions in a microarray format.

Depending upon the results of the cell culture, wells of interest can be identified and their contents selectively retrieved for further study and analysis. For example, wells showing enhancement or suppression of focal species function indicating a positive or antagonistic interaction can be extracted and the antagonizing or promoting species can be characterized and/or sequenced (e.g., 16S rRNA sequencing) for identification. The process can be repeated for any one or more wells of interest on a selective basis without disturbing adjacent wells.

Ultimately, selective and targeted portions or areas of the crosslinked hydrogel membrane 16' are then removed by exposure to radiation (light) of the appropriate wavelength, which decrosslinks at least a targeted portion of the hydrogel matrix. The sealed substrate 10 may remain immersed in cell culture media during the light exposure process and/or may be removed from the media during this step. The present inventive process can be used with radiation of most wavelengths under 400 nm, but preferred wavelengths are selected from the group consisting of 365 nm, 248 nm, 193 nm, 157 nm, and 13.5 nm. Alternatively, IR light can be used in combination with up-conversion nanoparticles in the hydrogel matrix. These particles convert IR light to UV to cleave nitrobenzyl or other photolabile groups. In this way, IR light could instead be used as the photodegradation light source. Exposure dosages are preferably minimized to reduce the possibility for inducing mutations and/or killing the microbes in the well via UV radiation. Suitable dosages will range from 0.1 mW/mm$^2$ to 5 mW/mm$^2$, preferably 0.5 mW/mm$^2$ to about 3 mW/mm$^2$, more preferably from about 0.5 mW/mm$^2$ to about 2 mW/mm$^2$, and even more preferably from about 0.5 mW/mm$^2$ to about 1.5 mW/mm$^2$. It will be appreciated that these parameters may be modified for different hydrogel systems.

In one embodiment, direct patterning light exposure systems can be used, which rely on computer-programmed spatial distribution of light to directly generate a specified and delimited light pattern from the light source (e.g., LED light) onto the crosslinked hydrogel membrane 16' without any use of masks or physical contact with the crosslinked hydrogel membrane 16'. Alternatively, as shown in FIG. 1(D), the crosslinked hydrogel membrane 16' could optionally be exposed using a mask 18 positioned above the crosslinked hydrogel membrane 16'. The mask 18 has open areas 18a designed to permit radiation (uv) to pass through the mask 18 and contact the crosslinked hydrogel membrane 16' to yield exposed portions of the crosslinked hydrogel membrane 16' that are rendered soluble. The remaining solid portions 18b of the mask 18 are designed to prevent radiation from contacting the crosslinked hydrogel membrane 16' in certain areas to yield unexposed portions of the crosslinked hydrogel membrane 16' that remain crosslinked (intact). Those skilled in the art will readily understand that the arrangement of open areas 18a and solid portions 18b is designed based upon the desired pattern to be formed in the crosslinked hydrogel membrane 16'. In particular, the open areas 18a of the mask will generally be aligned with (i.e., lined up over) one or more wells of interest for exposure and selective retrieval of that well's contents. In one or more embodiments, the photomask is preferably a dark field mask and is used to protect a large portion of the crosslinked hydrogel membrane 16' from exposure, while only a small portion of the crosslinked hydrogel membrane 16' (above the well of interest) is exposed at a time.

Regardless of whether direct light patterning is used or an optional photomask is used, upon exposure, the portions of the crosslinked hydrogel membrane 16' that are exposed to radiation are decrosslinked and come apart (disintegrate) to expose the microwell 12 underneath and release the target microbes 14', as shown in FIG. 1(E). Advantageously, because of the selective exposure process, the unexposed portions of the crosslinked hydrogel membrane 16' remain crosslinked and thus continue to seal off the remaining wells 12 in the substrate. As demonstrated in the working examples, this process can be used to expose wells individually, one at a time, as well as groupings of multiple wells according to any desired pattern. Further, this process could also be used to uncover one or more wells in combination with patterning one or more channels in the crosslinked hydrogel membrane 16' to guide the path of motile microbes out of the well 12 to the desired location (e.g., another well on the substrate, another device, such as an adjacent microfluidics device, etc.). In this way, the target microbes 14' can be selectively retrieved and moved to another apparatus, such as a new well, cell culture device or sequencer without contamination or human intervention. It will be appreciated that this process is particularly amenable to computer programmed and robotic handling systems for running the assays and subsequent retrieval and analysis of target microbes without human intervention.

Various exposure patterns can be used to induce decrosslinking and provide access to the microbes 14' in the well of interest. For example, in one or more embodiments, substantially the entire surface area of the crosslinked hydrogel membrane 16' above the well of interest can be exposed (e.g., a solid circle or square portion of corresponding size/shape as the opening of the well of interest). In this approach, substantially the entire portion of the crosslinked hydrogel membrane 16' above the well of interest disintegrates and exposes substantially the entire opening of the well of interest, as depicted in FIG. 1(D). Alternatively, perimeter-only illumination can be used, wherein only the portion of the crosslinked hydrogel membrane 16' above the well of interest generally corresponding to the perimeter of the opening is exposed. For example, in the case of a round microwell opening, an annular exposure pattern would be used (or a hollow square in the case of square microwells). In this way, only the edges of the exposed area disintegrate, leaving an unexposed central portion (or "island") within the exposed perimeter crosslinked. This central portion can be removed (e.g., peeled away), or simply moved to the side for retrieval of the well contents. In one or more embodiments, the microplate can be exposed while still immersed in cell culture media, which facilitates dissolution of the exposed portions of the membrane 16'. In a further embodiment, the exposure pattern can be designed to only expose a very small area above the well of interest so as to effectively "poke a hole" in the membrane of a size sufficient for the microbes to migrate out of the well, without necessarily exposing the entire well opening. Further, exposure dosages and/or the membrane itself can also be tuned to merely weaken or partially decrosslink the crosslinked hydrogel membrane 16' above the well of interest. This can either render the crosslinked hydrogel membrane 16' above the well of interest susceptible to faster degradation by the microbes in the well and/or cause the polymer linkages within the hydrogel matrix to expand thereby creating holes in the membrane of a size sufficient for the microbes to migrate out of the well.

After at least some portion of the well of interest has been uncovered by exposing the adjacent portion of crosslinked hydrogel membrane 16', the target microbes 14' in that well can then be retrieved. As noted in the examples, the microbes have a tendency to move fairly quickly out of the opened wells on their own, particularly if the microplate is immersed in culture media. Various approaches can be used for retrieving the microbes from the opened wells. As noted, the patterning process itself can be used to define channels in the crosslinked hydrogel membrane 16' to guide the microbes along a defined path. For example, the microbes could be guided to an adjacent microfluidics device. Another method involves washing the wells with a buffer to detach them from the wells. Another approach involves microcontact printing where the opened wells are stamped or contacted in face-to-face engagement with an agar plate into which the microbes move, followed by removal of the agar plate (and thus the contents of the well). The microbes can also be simply pipetted out of the microwells. In one or more embodiments, the bottom wall and well sidewalls can be made of non-adherent material and/or surface treated to reduce cell adhesion if desired. After retrieval, the target microbes 14' can be further analyzed and studied as desired.

The foregoing process is described primarily in relation to a microwell plate. However, it will be appreciated that the crosslinked hydrogel membrane 16' could be similarly applied to cover microchannels in a microfluidics device. Likewise, the microwell plate described above could be paired with a microfluidics devices for further study of the target microbes. Microfluidic devices general comprise a cartridge and a planar substrate retained in the cartridge. The cartridge comprises a sample inlet well formed in the cartridge above a sample application region in or on the substrate and at least one detection region in fluid communication with the sample application region via a microfluidic channel extending from the sample application region to the detection region. The microfluidic channel has a terminal end positioned distal from the inlet well, and an optional absorbent pad positioned at the terminal end (to facilitate flow of the sample completely through the channel). Microfluidics devices are generally designed to handle very small sample volumes (e.g., from about 10 µL to about 5 mL) that flow by capillary action through the microchannel(s) in the device and are further reduced, such that the detection region may generally have a volume of about 100 µL to about 1 µL.

The inventive approach is useful for investigating microbial behavior in a spatially confined environment. In some ecosystems, microbes exist in a microporous, spatially-confined environments (e.g., soil, tissue). Placing microbes in microscale geometries such as microwell arrays allows one to mimic and study certain aspects of the microbe's "natural" environment, such as growth in a diffusion limited environment. The approach is also useful for micro-ecology patches, which are microfluidic devices made for studying microbial interactions in controlled physical and chemical environments. There is often a need to extract out of these devices to further characterize the microbes. The current approach also finds possible use in drug delivery. Photodegradable hydrogels have been developed for delivery of proteins and/or other therapeutics, which could likewise be applied for delivery of beneficial microbes as human therapies. The hydrogels can be used to protect the microbes as they move through the body, followed by localized light exposure to release the hydrogel in the targeted location. This approach would particularly benefit from IR-light degraded embodiments. It will be appreciated that essentially any microwell format for observing/screening bacteria or other microbe populations can be improved by use of the inventive hydrogel and targeted retrieval process.

Additional advantages of the various embodiments of the invention will be apparent to those skilled in the art upon review of the disclosure herein and the working examples below. It will be appreciated that the various embodiments described herein are not necessarily mutually exclusive unless otherwise indicated herein. For example, a feature described or depicted in one embodiment may also be included in other embodiments, but is not necessarily included. Thus, the present invention encompasses a variety of combinations and/or integrations of the specific embodiments described herein.

As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

Further, while the drawings illustrate, and the specification describes, certain preferred embodiments of the invention, it is to be understood that such disclosure is by way of example only. Embodiments of the present invention are described herein with reference to cross-section illustrations that are schematic illustrations of idealized embodiments of the present invention. As such, variations from the shapes of the illustrations as a result, for example, of manufacturing techniques and/or tolerances, are to be expected. There is no intent to limit the principles of the present invention to the particular disclosed embodiments. For example, in the drawings, the size and relative sizes of layers and regions may be exaggerated for clarity. In addition, embodiments of the present invention should not be construed as limited to the particular shapes of regions illustrated herein but are to include deviations in shapes that result, for example, from manufacturing. For example, an etched region illustrated as a rectangle may have rounded or curved features. Thus, the regions illustrated in the figures are schematic in nature and their shapes are not intended to illustrate the precise shape of a region of a device and are not intended to limit the scope of the present invention, unless otherwise indicated.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

EXAMPLES

The following examples set forth methods in accordance with the invention. It is to be understood, however, that these examples are provided by way of illustration and nothing therein should be taken as a limitation upon the overall scope of the invention.

Figure 2A:
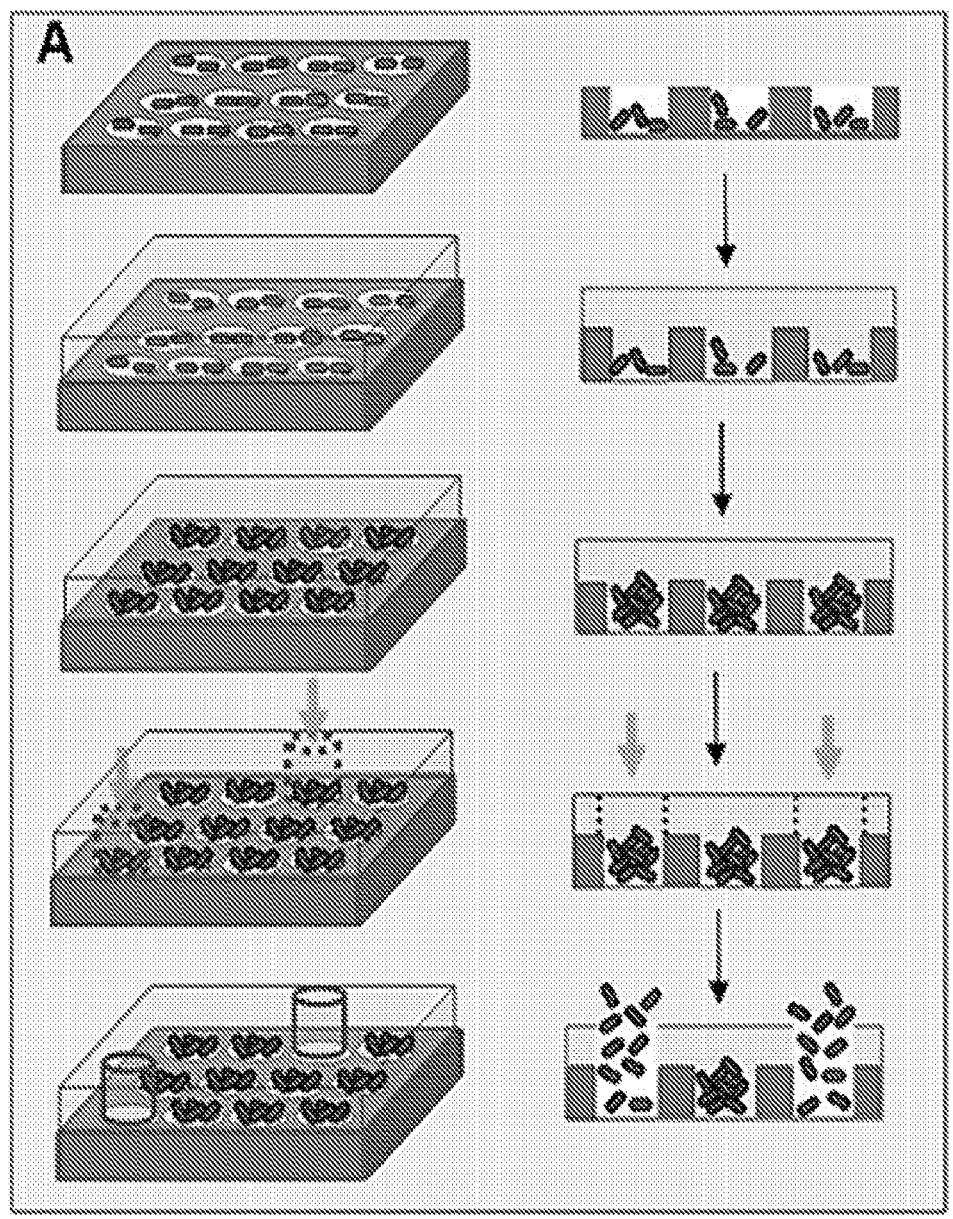
FIG. 2A illustrates the described technique of on-demand release and retrieval of bacteria from microwell arrays using a photodegradable membrane, in which the microwell array is seeded with fluorescent cells that are confined to the wells by attaching a membrane that supports cell growth. Irradiation with light (light arrows) degrades the membrane and opens selected microwells after which cells can be retrieved.

On Demand Release and Retrieval of Bacteria from Microwell Arrays Using Photodegradable Hydrogel Membranes Introduction An important feature of our platform for on-demand release of bacteria from microwell arrays is the attachment of a photodegradable membrane (green) on a silicon microarray (blue) that traps motile, live cells (red) in wells (FIG. 2A). The membrane forms a physical barrier that prevents bacteria from escaping the microwells but allows diffusion of nutrients, oxygen, and metabolic waste products. The membrane can also be locally degraded by bacteria to generate space for growth within the wells. Light irradiation of selected microwells opens the wells allowing for retrieval and characterization of the present cells (FIG. 2A).

Figure 2B:
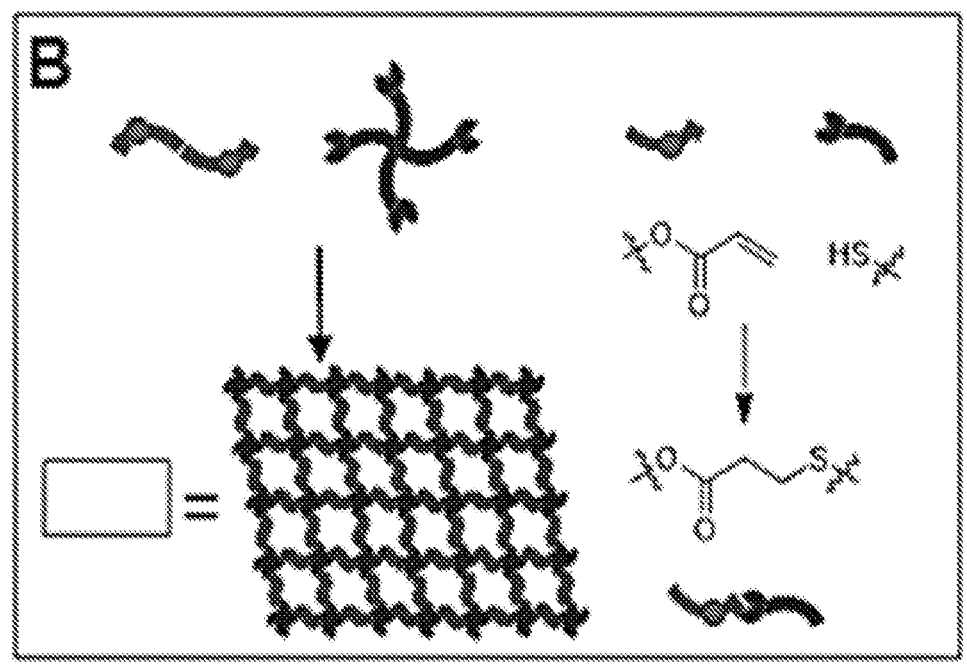
FIG. 2B is an illustration of the polymerization and crosslinking of the photodegradable membrane made by reacting a four arm PEG-thiol with a photodegradable PEG diacrylate by a Michael-type addition reaction.
Figure 2C:
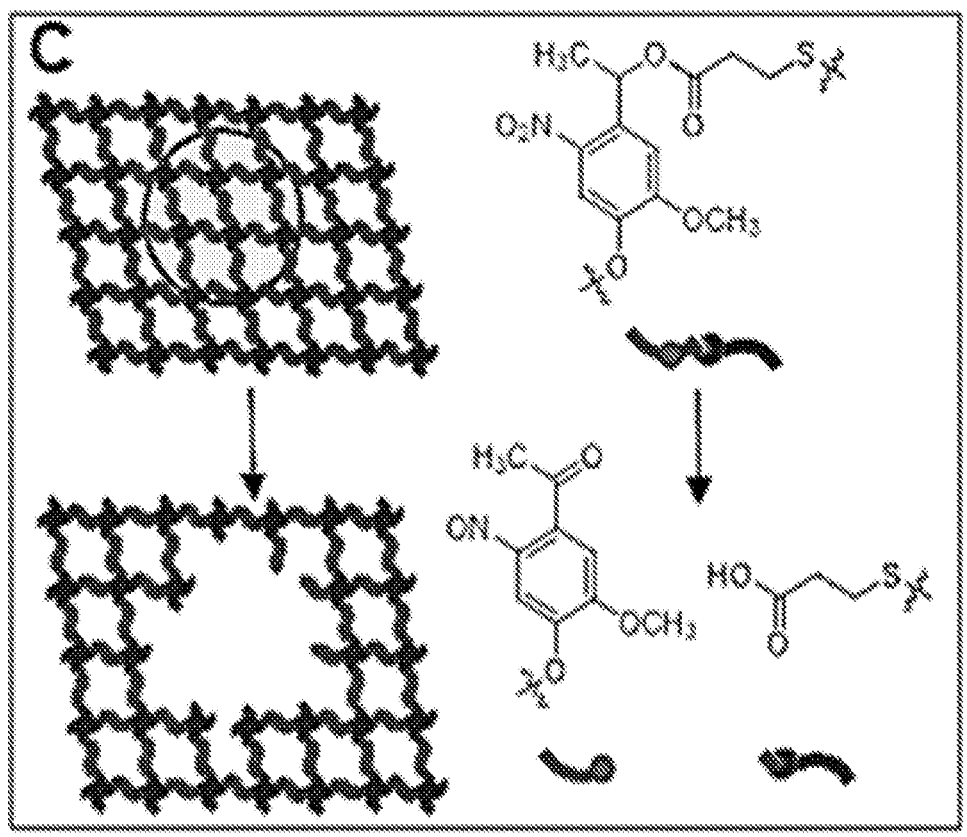
FIG. 2C is an illustration of the polymer network of the membrane being degraded when the photodegradable nitrobenzyl group present in the crosslinks is cleaved by patterned light (circle) and the polymeric reaction products dissolve in the aqueous medium.

In this work, we explore photodegradable hydrogels using the thiol-acrylate Michael-type addition reaction between functionalized multi-arm PEG polymers. The photo-degradability of these hydrogels stems from the incorporation of a light-cleavable nitrobenzyl group within their network structure, which allows for a controlled decrease in crosslinking density throughout the network upon light exposure to the point of reverse-gelation. These materials allow for high spatiotemporal control over degradation, are non-toxic to cells, and their aqueous nature permits transport of nutrients and waste products to support bacterial cell growth within microwells. For these reasons, we identified photodegradable PEG hydrogels as a good material for use as responsive membranes over microwells to demonstrate the proof of concept. To generate membranes, a step-growth polymerization mechanism that uses a tetra-functional PEG-thiol crosslinker and a photodegradable PEG-diacrylate was used (FIG. 2B). A key advantage of this polymerization approach is that it generates hydrogel networks with uniform crosslinking density and microstructure, allowing for uniform diffusion across the array.

Membrane Attachment

Figure 3:
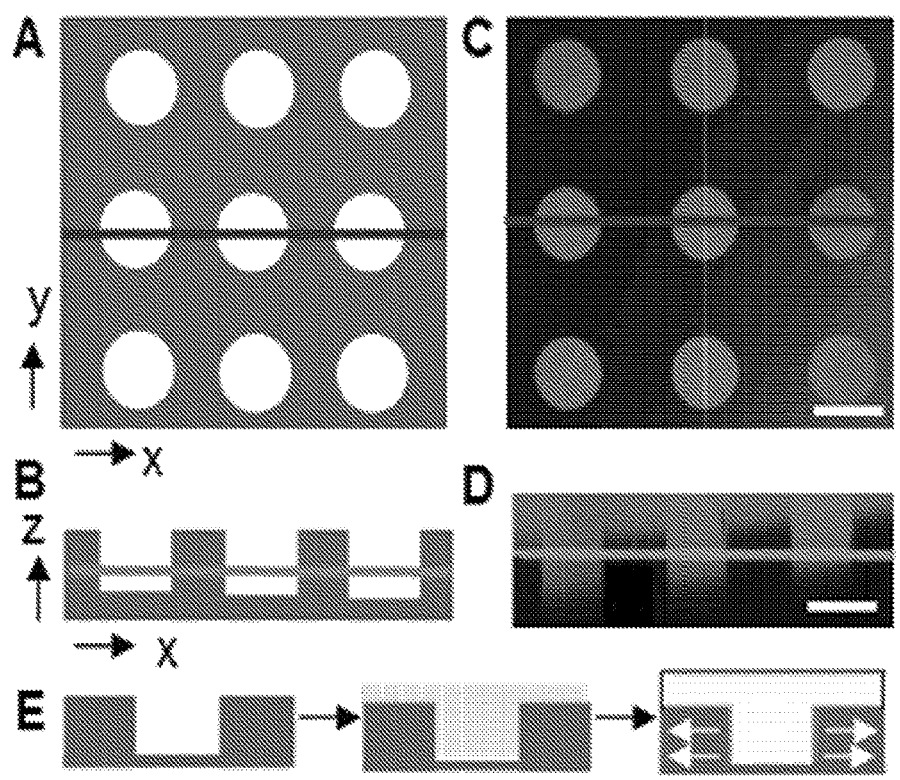
FIG. 3 shows schematic representations and corresponding confocal images of the membrane attached to a microwell array. (A) Schematic representations of the microwell viewed in the xy plane; (B) Schematic representations of the microwell viewed in the xy plane; (C) Confocal image showing fluorescence signal, indicating fluorescein labeling of the PEG hydrogel membrane, coming from the xy plane along the green line in the xz plot shown in (D); (D) Confocal image showing fluorescence signal coming from the xz plane along the red line shown in the xy plot (C); (E) Proposed locking mechanism for membrane attachment. The membrane precursor solution mixes with culture medium in well and crosslinks to form the hydrogel; and when placed in culture medium the membrane swells creating forces on the walls of the microwells preventing detachment. Microwell size: 100 µm, scale bar: 100 µm.

To test the attachment strategy, microwells were first filled with LB medium, followed by applying the hydrogel precursor solution. Upon removing the glass slide, the membrane remained firmly attached to the microwells and no membrane movement was observed after incubating the array in LB medium for 2 days. The density of microwells appeared to be a factor promoting stable membrane attachment, as membrane detachment occurred within several hours when microwell arrays with lower well densities where placed in LB medium. To verify that membrane attachment occurred through an anchoring mechanism, we used confocal laser scanning microscopy to obtain three-dimensional reconstructions of fluorescently-labeled membranes on microwell arrays (FIG. 3C and FIG. 3D). Due to its non-fluorescence, the silicon microwell array appears black whereas the membrane appears green after labeling the membrane with fluorescein. The membrane is present throughout microwells with observed diameters (100 µm) and depths (20 µm) that correspond to well dimensions (FIG. 3). Similar results were obtained for microwells with 4, 20, 40, 50 and 60 µm diameters (data not shown). Swelling of the membrane was confirmed by measuring membrane thickness after arrays were placed in LB medium. Hydrogels were observed to be approximately 150 µm thick despite having been polymerized on microwell arrays using 38 µm spacers, suggesting that swelling had occurred.

Membrane-Bacteria Characterization

Figure 4:
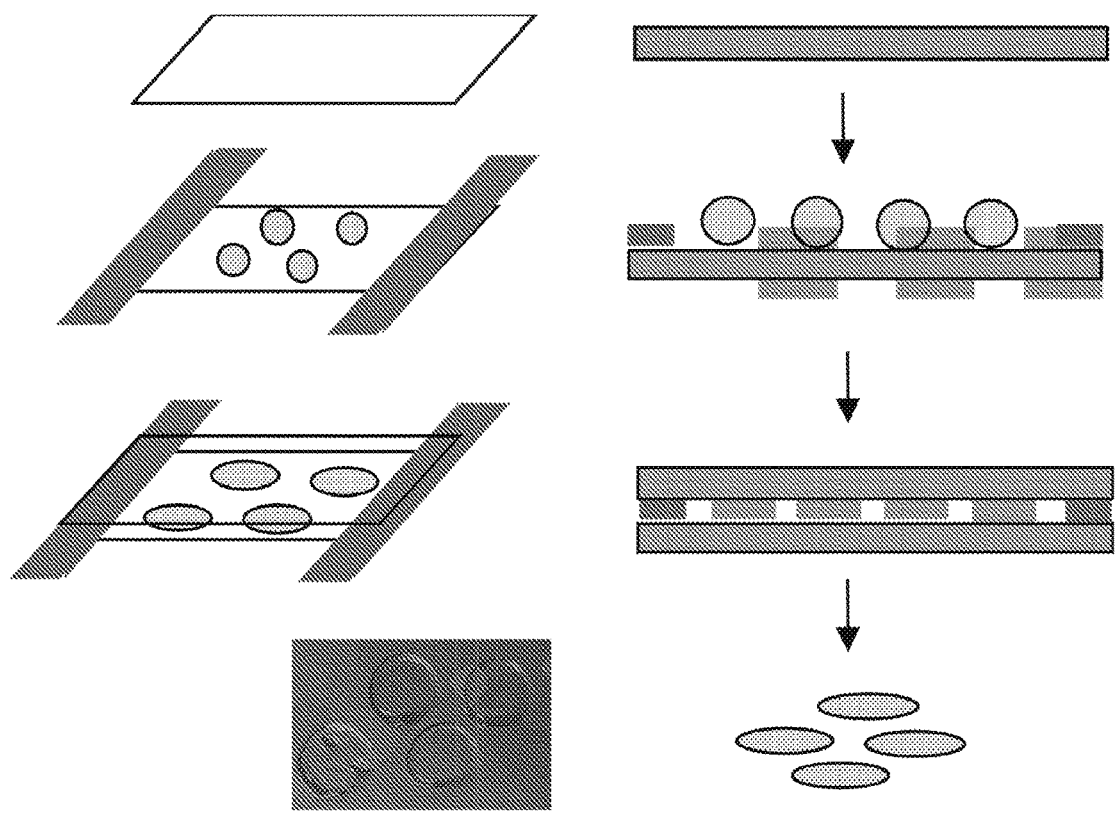
FIG. 4 is a schematic representation of the setup for the fabrication of *A. tumefaciens*-encapsulated membranes sandwiched between two glass slides, and a photograph of the hydrogels formed.
Figure 5:
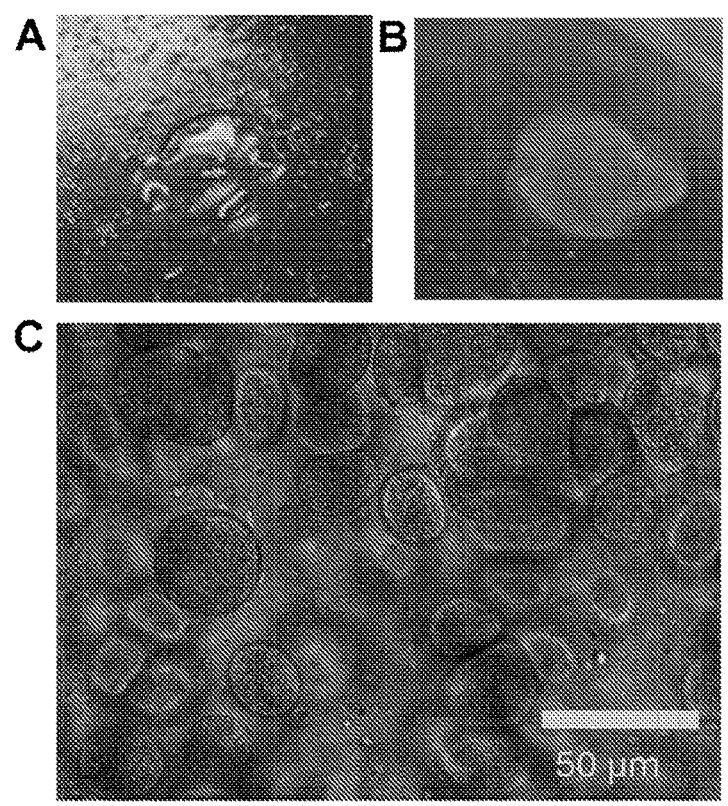
FIG. 5 shows photographic images confirming that *A. tumefaciens* can grow inside the hydrogel material: (A) Photograph of a membrane with encapsulated *A. tumefaciens* on an agar plate immediately after washing; (B) The same membrane after 24 hours at 28° C. showing that the initial clear membrane has an opaque appearance due to growing bacteria; and (C) Microscope image of the same membrane showing the presence of *A. tumefaciens* clusters 20-40 µm in size.
Figure 6:
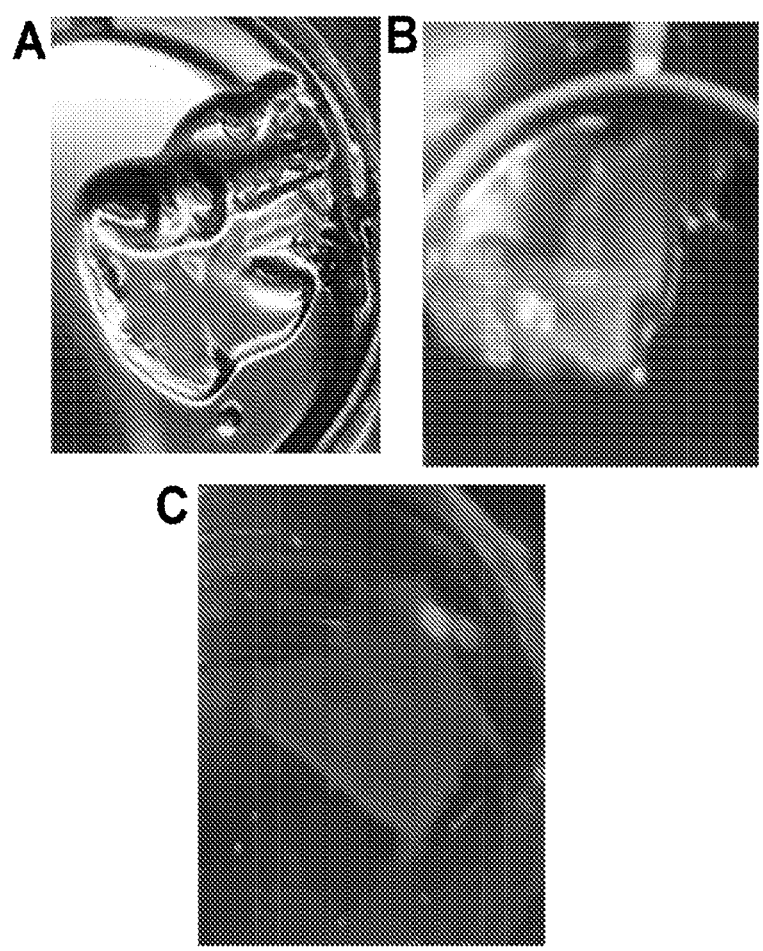
FIG. 6 shows photographs of the cell viability test using TTC to show that the bacteria inside the hydrogel are alive: (A) *A. tumefaciens*-encapsulated hydrogel after crosslinking and swelling in liquid LB medium; (B) The same membrane but 24 hours later; and (C) The same membrane after another 24 hours cultured in the presence of TTC, which is reduced by metabolically active bacteria resulting in formation of pink water-insoluble crystals.
Figure 7:
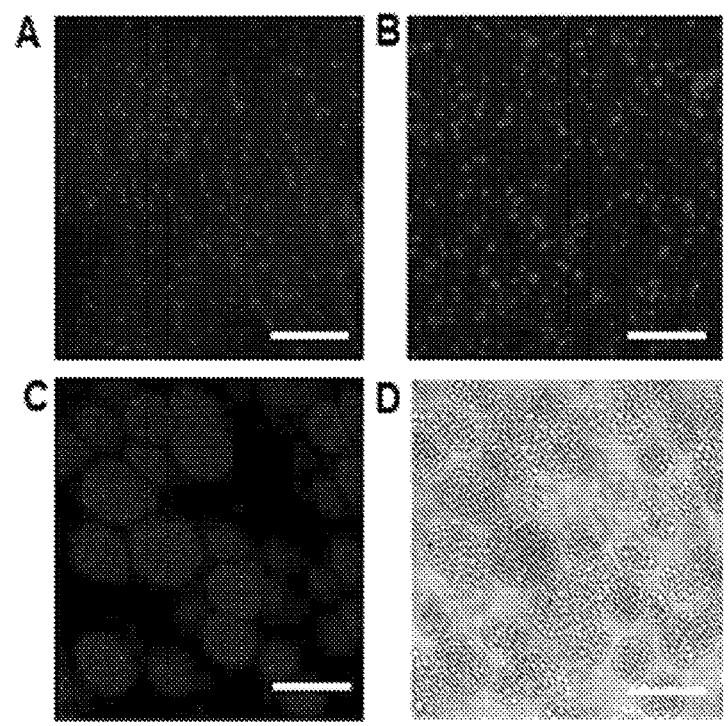
FIG. 7 shows confocal images of *A. tumefaciens* fixed for fluoresce imaging after encapsulation inside the hydrogel for different periods of time: (A) 0 hours; (B) 10 hours; (C) 24 hours; and (D) a differential interference contrast (DIC) image at 24 hours. Scale bar: 50 µm.

A potential limitation to attaching the membrane to the microwells via the anchoring mechanism is that the membrane may occupy well space required for bacterial growth. However, these photodegradable PEG hydrogels have ester groups in the crosslinks which can be degraded via hydrolysis and allow for bacteria-dependent network degradation. Consequently, bacteria embedded within the hydrogel membrane should be able to grow within spaces that they create by locally degrading the membrane. To test this, we encapsulated *A. tumefaciens* cells expressing the fluorescent protein mCherry by adding the cells to the membrane precursor solution (FIG. 4). A suspension of bacteria in 2× LB are mixed with solutions of the precursor solution (pH 8, acrylate/thiol concentration 22 or 35 mM) and pipetted onto a glass slide (spheres) having spacers opposite of each other. Immediately a second glass slide is placed on top and the crosslinking reaction was carried out at room temperature for 25 minutes. After carefully separating the glass slides the bacteria-encapsulated membranes are washed and kept on agar or in liquid culture medium at 28° C. After gelation, individual bacteria cells encapsulated within the gel could be observed by microscopy (data not shown). After 24 hours, the membrane itself appeared opaque (FIG. 5A and S2B) indicating that bacteria had grown within the gel. This was confirmed by microscopy which showed the presence of large (20-40 µm) clusters of cells (FIG. 5C). These clusters also formed inside membranes prepared at higher thiol/acrylate concentrations (Thiol concentration: 35 mM, acrylate concentration: 35 mM) (FIG. 7, FIG. 6A and FIG. 6B). Membranes were fixed at different time points to see how the initial single bacteria grow into larger clusters over the course of 1 day. To confirm that the bacteria inside these clusters were alive after 24 hours, unfixed membranes were placed in LB containing triphenyltetrazolium chloride (TTC). This compound is colorless but is reduced by metabolically active bacteria resulting in the formation of pink water-insoluble crystals. When TTC was added, the gel turned pink and microscopic observation showed the presence of crystals showing that the bacteria in the clusters were alive (FIG. 6C).

The mesh size of PEG hydrogels is typically in the nanometer range. For this reason, it is unlikely that the space occupied by the observed clusters of bacterial cells (FIG. 7) was initially present in the membrane. The presence of the large clusters also shows that the mesh size of the membrane does not cause mass transfer limitations of nutrients. PEG hydrogels formed with higher polymer concentrations and a smaller mesh size also supported the formation of large clusters of viable bacteria (data not shown).

Culture of Cells in Microwell Arrays with Attached Hydrogel Membranes

Figure 8:
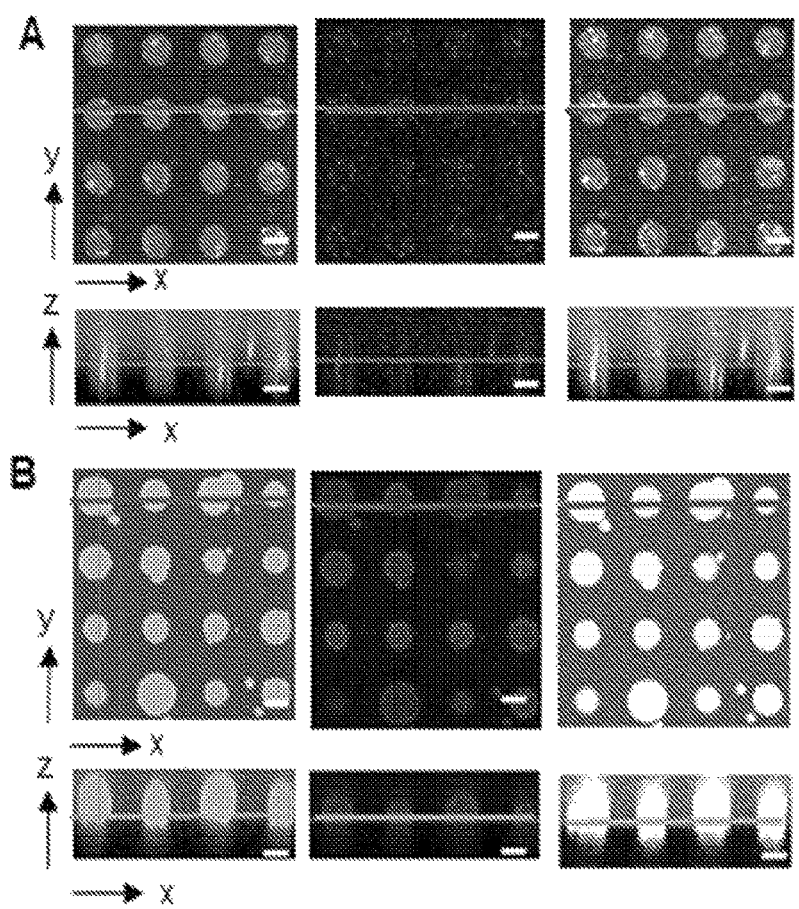
FIG. 8 shows confocal images of *A. tumefaciens*-seeded microwell array with an attached hydrogel membrane. (A) Fluorescence intensities 3 hours after cell seeding coming from the xy plane along the green line and the xz plane along the red line. Left panel: green fluorescence fluorescein-labeled membrane, middle panel: red fluorescence of the bacteria, right panel: overlay of both. (B) The same as (A) but after culturing for 24 hours. Samples were fixed prior to measurements. Well diameter: 20 µm, seeding OD=0.2, scale bar: 20 µm.

Our platform requires that the photodegradable membrane both prevents cells from leaving microwells but does not interfere with cell growth. Three hours after seeding cells into 20 µm diameter wells, fluorescein-labeling of the hydrogel shows that the membrane is present throughout these microwells with localized spots of higher fluorescence intensity (FIG. 8A, left panel). These spots spatially correspond to the location of the seeded bacteria (FIG. 8A, middle and right panels). We propose that reaction of fluorescein maleimide with thiol groups present on the bacteria result in cells having fluorescent signal in both the green and red channels. To show that the bacteria can grow with the membrane attached to the array, we seeded *A. tumefaciens* at the same optical density but kept the microwell immersed in medium for 24 hours. Consistent with bacterial growth, there is an increase in the red fluorescence signal following this incubation (FIG. 8B, middle panel). Further, bacteria are present above the silicon/membrane interface (FIG. 8B, middle and right panels). Although 38 µm spacers were used during hydrogel preparation, the thickness of the membrane is much greater due to swelling of the membrane in the culture medium (approximately 150 µm thick). Bacteria are present approximately 40 µm above this interface, indicating that bacteria can invade the membrane. However, membrane degradation appears localized such that there is no mixing between neighboring wells over the 24 hour time period required for growth (FIG. 8B). These observations indicate that the membrane polymerized over a seeded microwell array serves as an effective barrier that compartmentalizes the microwells while allowing bacteria to proliferate inside of the microwells—a critical requirement when screening for growth or growth inhibition in screening applications.

Membrane Photodegradation and Cell Release

Figure 9:
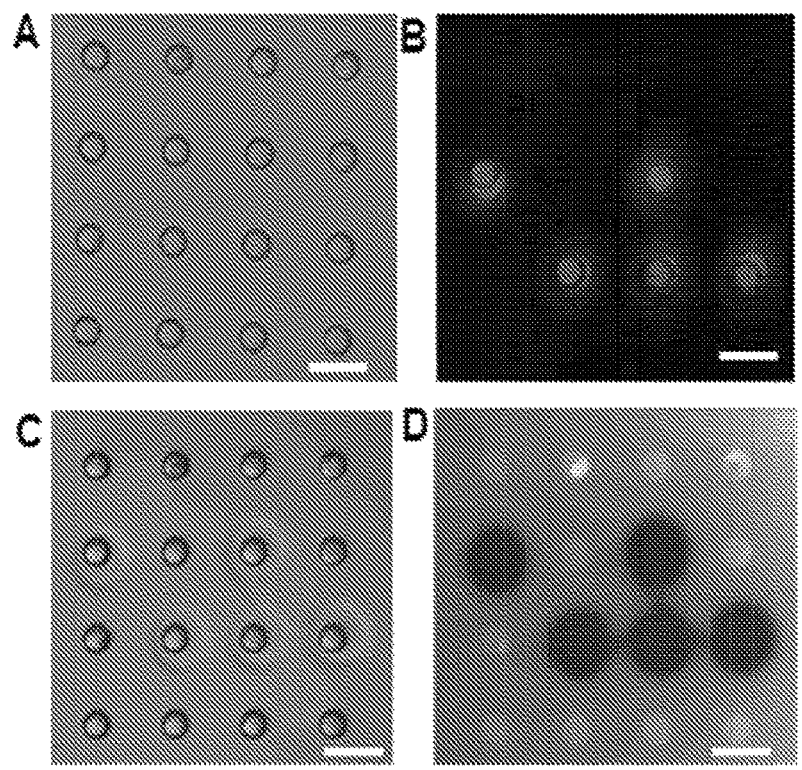
FIG. 9 confocal images showing that microwells can be opened by degrading the membrane with light. (A) 45 µm wells after membrane attachment, (B) during irradiation, (C) after irradiation (D) and after labeling with fluorescein maleimide. Exposed area: 50 µm diameter circle, Irradiation time: 5 minutes, light output: 1.4 mW/mm$^2$. Scale bar: 100 µm.

The ability to selectively open microwells is critical for bacteria retrieval. To demonstrate this, we used patterned illumination with the Polygon400 to degrade the membrane over, and thereby open targeted 45 µm diameter microwells (FIG. 9). To confirm membrane degradation has occurred only in irradiated areas, the membrane was labeled with the thiol-reactive fluorescein maleimide dye and observed by fluorescence microscopy. Irradiated areas are devoid of fluorescent signal indicating that polymer network degradation is localized to directly irradiated areas.

Figure 10:
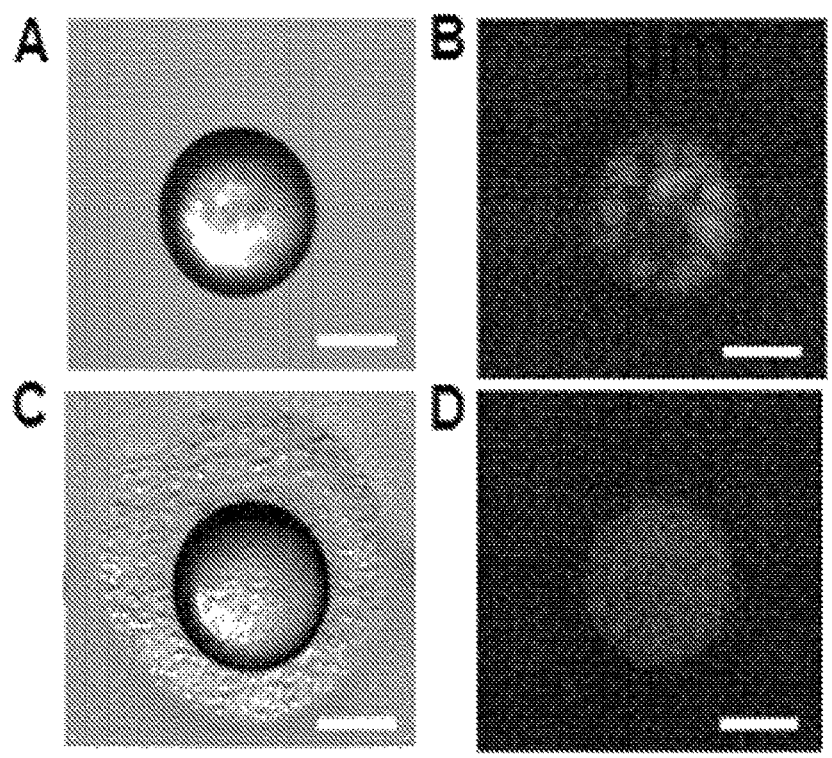
FIG. 10 Bright field and fluorescence images evidencing membrane degradation of bacteria-seeded microwells leads to bacteria release. (A) and (B) show images before irradiation; and (C) and (D) show images after irradiating a 60 µm microwell with the Polygon400; scale bar: 30 µm.

To demonstrate the ability to release bacteria from microwells, *A. tumefaciens* was seeded at OD=0.2 and cultured for 2 days in 60 µm wells. The membrane was then irradiated with light (FIG. 10), using an exposed area of a 120 µm circle, irradiation time: 5 minutes, light output: 2 mW/mm$^2$. The polymer network degrades, opens the microwells, and releases cells. A few minutes after light exposure, bacteria move to the irradiated area next to the microwell (FIG. 10C) while other cells stay in their microwell (FIG. 10D). Notably, localized clusters of cell fluorescence present within microwells prior to irradiation (FIG. 10B) are no longer visible after irradiation. Instead the fluorescence signal observed within irradiated microwells appears diffuse, suggesting that cells are no longer structured into clusters by the hydrogel (FIG. 10D).

Figure 11:
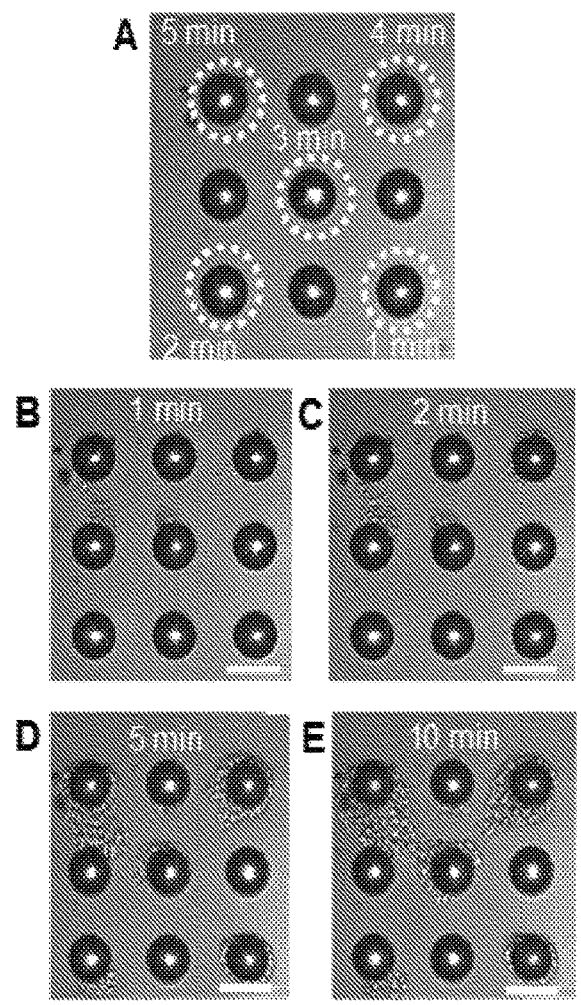
FIG. 11 shows bright field images evidencing the effect of irradiation time on bacteria release from 20 µm diameter wells. Wells were irradiated as indicated for either 1, 2, 3, 4, or 5 minutes (A) and afterwards observed over the course of 10 minutes (B)-(D). Light output 0.7 mW/mm$^2$; Scale bar: 25 µm.

The Polygon400 allows spatiotemporal control over membrane degradation. To examine how irradiation time at a fixed light intensity impacts bacteria release from 20 μm diameter microwells, we irradiated adjacent microwells for 1, 2, 3, 4, or 5 minutes (FIG. 11A). Cells were observed moving out of all of these wells by 5 minutes after irradiation (FIG. 11D), however cells were observed exiting microwells that were irradiated for longer periods of time only 1 or 2 minutes after irradiation (FIG. 11B and FIG. 11C).

Figure 12:
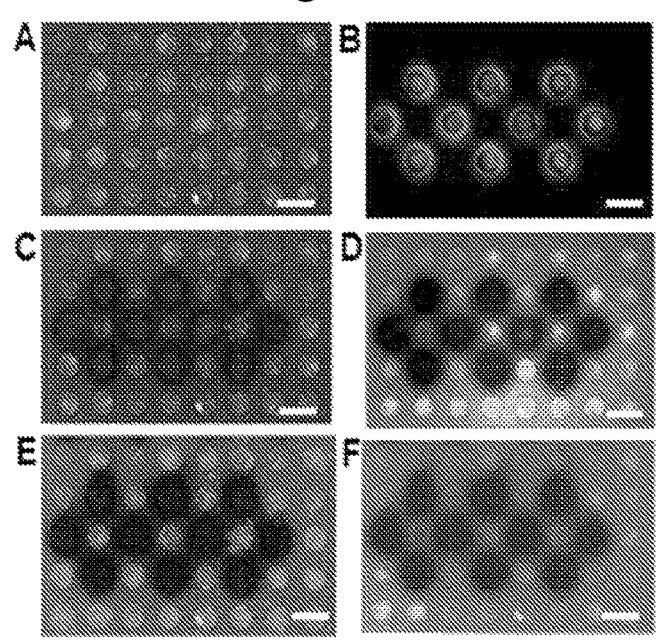
FIG. 12 shows fluorescence images evidencing that several wells can be opened simultaneously using the Polygon400. (A) *A. tumefaciens* expressing fluorescent mCherry was seeded at OD=0.2 and cultured for 1 day. (B) Simultaneous irradiation of ten 50 µm microwells with a 60 µm circle pattern for 5 minutes at 0.7 mW/mm$^2$. (C) Microwells that were irradiated show diffuse red fluorescence due to the moving bacteria. (D) Fluorescein maleimide labeling confirms membrane degradation (E) and (F) the same as (C) and (D) but after washing with LB medium. Scale bar: 100 μm.

A benefit of this method is that any number and combination of wells can be simultaneously opened, enabling parallel extraction of cell populations, if desired. To demonstrate this, ten nearby 50 μm diameter microwells were simultaneously irradiated using the Polygon400 (FIG. 12A and FIG. 12B), resulting in cell release (FIG. 12C and FIG. 12E) and membrane degradation (FIG. 12D and FIG. 12F) from each targeted well. The cell dependent fluorescence signal drops to background levels after washing the microwells with LB medium showing that the bacteria can be removed (FIG. 12E).

Retrieval of Bacterial

Figure 13:
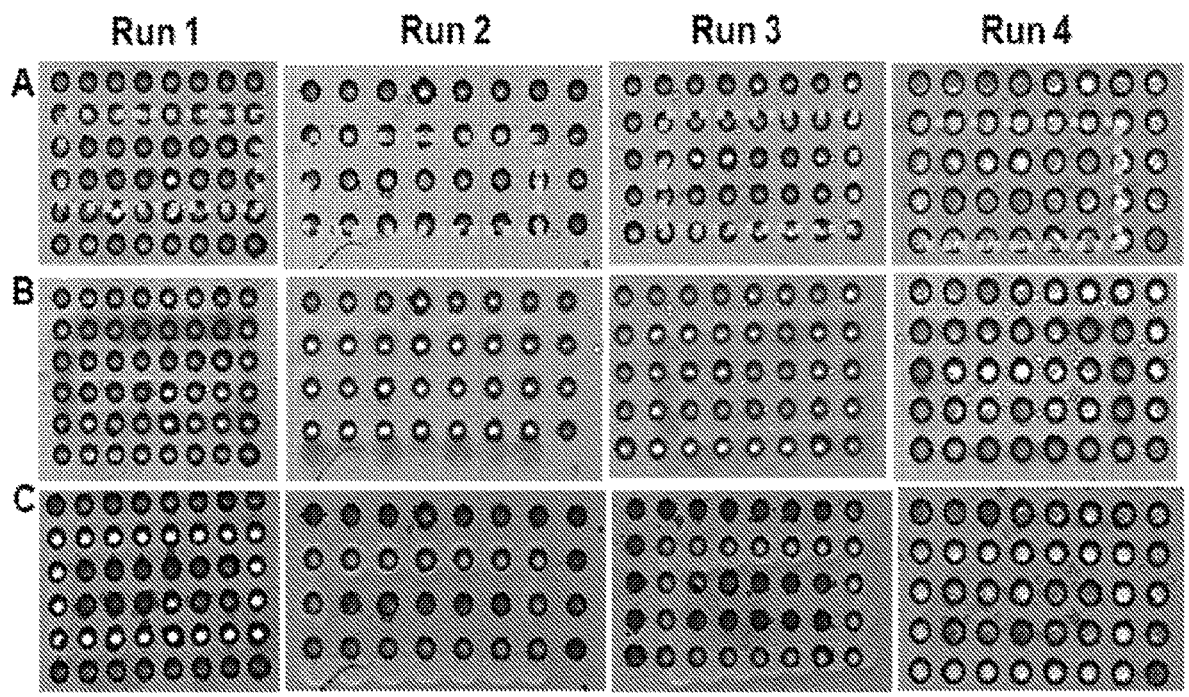
FIG. 13 shows brightfield images showing a total of 72 microwells that have been opened with light. (A) Microwells before irradiation (B) The same microwells immediately after irradiation and (C) The same microwells after washing with Tween20/LB. 40 μm diameter (runs 1-3) and 50 μm diameter (run 4) microwells were irradiated with 60 μm circle patterns for 5 minutes at 0.7 mW/mm$^2$.
Figure 14:
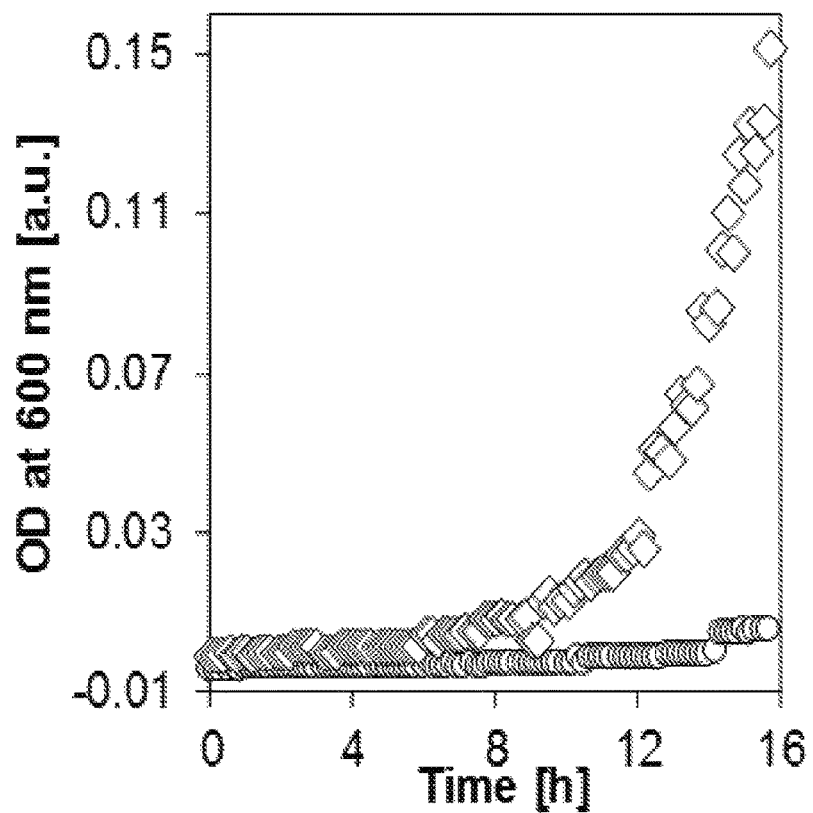
FIG. 14 is a graph of the growth curve of *A. tumefaciens* isolated from microwells using the inventive technique.

To verify that bacteria from selected wells can be harvested from wells and cultured for follow-up analysis, opened wells were washed with an extraction medium. Washing after well opening is an easy and straightforward approach to retrieve cells, since the other wells remain sealed. Additionally, this approach allows easy verification that bacteria have been extracted by using a microscope to inspect washed microwell arrays (e.g., FIG. 12E). To show that we can retrieve bacteria from selected microwells, 72 microwells (40-50 μm in diameter) were opened in four different runs (FIG. 13). A. tumefaciens was seeded at OD=0.2 and cultured for 1 day at 28° C. before irradiation. The arrays were then washed with extraction medium (LB with 0.05% Tween20) to remove the bacteria from the microwells. To show that the bacteria were viable and could be enriched, the washings were cultured overnight in a polystyrene well plate. As a control to show that the isolated bacteria originate from the opened microwells, the microwell array was also washed with the same volume of extraction medium prior to the well opening. The washings from opened wells indicate bacteria growth as measured by the increase in OD at 600 nm (FIG. 14). The bacteria are viable and can be cultured. A total of 72 microwells (40-50 μm in diameter) were opened with light. After careful washing of the membrane with LB with 0.05% Tween20, the solution was placed inside a plate reader and the OD tracked over time. Washings after opening the microwells (rhombus) show an increase in OD over the course of 16 hours. In contrast, the control washings before opening the microwells (circles) do not show bacterial growth and did not increase in OD over time (FIG. 14), suggesting that the bacteria cultured from washings after well opening originated from the opened microwells. These results demonstrate that bacteria can be retrieved from the microwells and grown in liquid culture for follow-up analysis.

Avoiding Direct Exposure of Bacteria to UV Light

Figure 15:
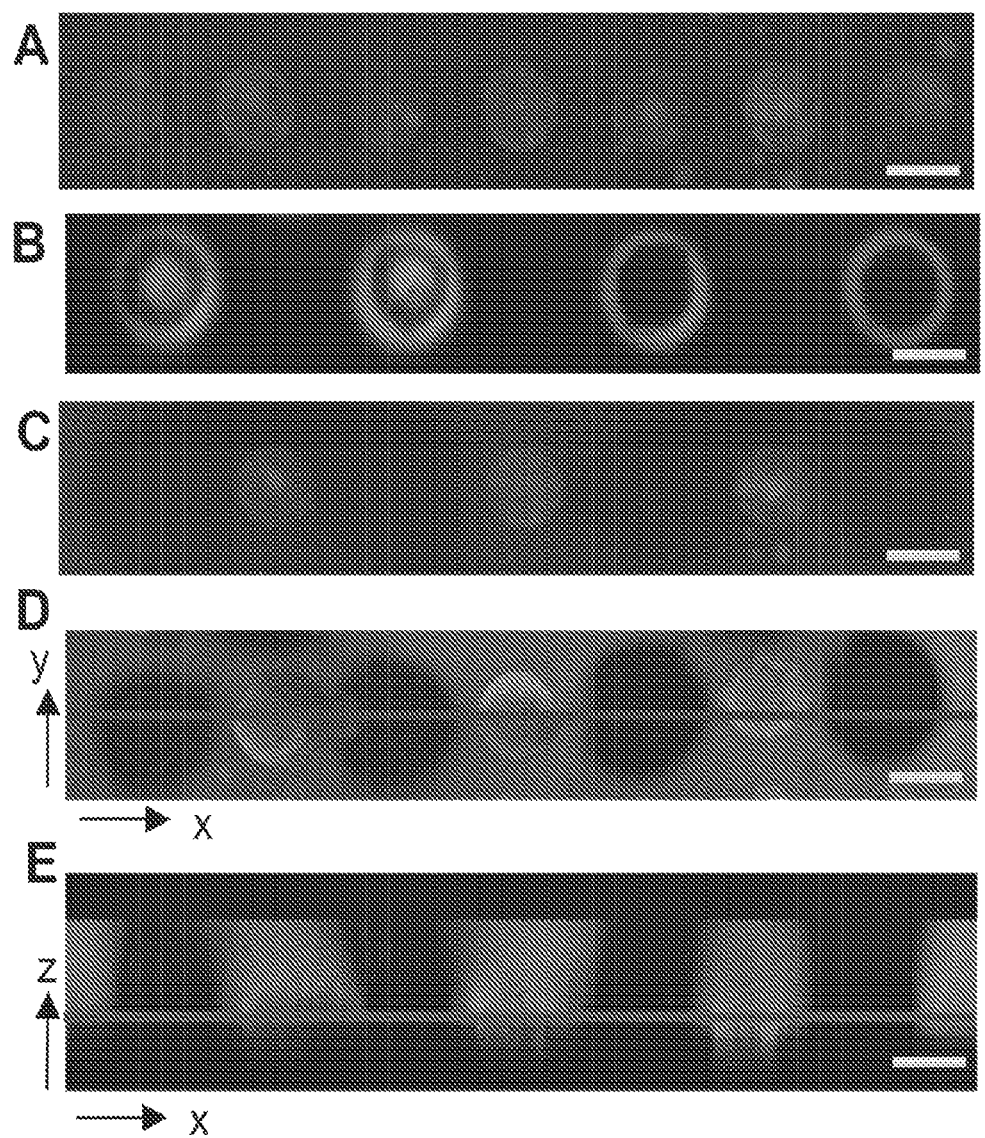
FIG. 15 fluorescence images showing the effect of light pattern on bacteria removal from microwells after culture for 1 day (OD=0.2 seeding density). (A) 40 μm microwells containing bacteria were (B) irradiated either with 60 μm light circle or 60/40 μm light ring patterns for 5 minutes at 0.7 mW/mm$^2$. (C) Cells are released as shown by the diffuse red fluorescence. After washing, the membrane is fixed and imaged by confocal microscopy. (D) Fluorescence signal (green indicating fluorescein-labeled membrane, red indicating cells expressing mCherry) coming from the xy plane along the green line in (E). (E) Fluorescence signal coming from the xz plane along the red line in (D). Scale bar: 40 μm.

One problem in applications using light for manipulating of cells is its effects on cell viability and behavior. In our inventive approach, light was projected in a ring pattern with an inner diameter corresponding to the diameter of the well. It was found that this approach can also release bacteria from the wells (FIG. 15A-C). Here, the membrane surrounding the perimeter of the well is removed, and the remaining membrane "island" likely diffuses into solution. This has the advantage that bacteria inside the wells are not directly exposed to UV light, thereby reducing the damaging effect of the light. We found that irradiation of 40 μm diameter microwells with either full light circles or light ring patterns resulted in loss of the membrane above the wells (FIG. 15D). In both cases, cells were moving freely as observed by the diffuse mCherry fluorescence patterns (FIG. 15C). To evaluate whether the pattern of light exposure influences cell retrieval, we washed the membrane with medium and fixed bacteria in the membrane on the microwell array and observed them by confocal microscopy (FIGS. 15D and 15E). Release of bacteria from wells irradiated with light ring patterns was indistinguishable from wells irradiated with full light circle patterns (FIGS. 15D and 15E). Thus, this new approach using perimeter-only illumination is an important feature in this approach, circumventing many of the limitations associated with using high intensity and longer exposure times.

Conclusions

The retrieval capabilities demonstrated here connect the high-throughput screening benefits inherent in microwell array formats with the ability to extract, isolate and enrich cells from any well of interest in order to acquire precise molecular information on that cell population. Ultimately, this platform opens up the door for characterizing cell populations that show a desired, unique, or rare function in a microwell screening assay at the genomic and transcriptomic level. The proof-of-principle studies demonstrated here show that the photo-responsive membrane attaches to microwell substrates, confines bacteria while allowing for nutrient exchange and cell growth, and is degradable with patterned light for cell release and retrieval from any well of interest at high (20 μm) spatial precision. Important design features are the presence of the photo-reactive group, allowing for photosensitive polymer network degradation, thereby opening of the wells in a spatially controlled manner using the Polygon400 pattern illumination instrument, and the ability to avoid direct exposure of cells to UV using patterned ring (perimeter-only) illumination. In our laboratory, these methodological advancements will be used for screening environmental microbes for antagonistic or synergistic impacts on bacteria of key functional importance, such as A. tumefaciens and other pathogens. Although our focus is on bacteria, the platform and method should be amendable for applications involving mammalian cells as well.

Materials and Methods

Instruments

All bright field and fluorescent microscopy images were taken with an upright (BX51, Olympus Japan) microscope equipped with a 3S camera (Luminara, Ottowa, ON, Canada) controlled by the Infinity Capture Software unless otherwise stated. For experiments involving the Polygon400 (Mightex Systems), the camera was controlled by the Mightex Polyscan2 software. Greyscale images were processed and colored using ImageJ software for visualization: blue for Polygon400 light patterns, red for mCherry and green for fluorescein.

Confocal Laser Scanning Fluorescence Microscopy (CLSFM) images were acquired on an Olympus FluoView FV1000-D confocal laser scanning fluorescence microscope equipped with 473 nm and 559 nm lasers and controlled by the Fluoview software.

Light patterns were projected onto the membrane using the Polygon400 instrument attached to the BX51 upright microscope via an adapter containing a dichroic/filter cube. The 365 nm high-power LED source (50 W) was controlled by a BioLED light source control module and delivered to the Polygon400 with a liquid light guide. A BioLED analog and digital I/O control module provided computer control and TTL trigger when used with the LED controller. Size and shape of the pattern, light intensity as well as irradiation time were controlled with the Mightex PolyScan2 software. Approximate light intensities for the 10×/0.3NA and 20×/0.5NA objectives according to the manufacturer are 7 and 20 mW/mm$^2$ respectively with the LED source at maximum intensity (100%). Prior to each experiment the Polygon400 was calibrated with a mirror and the calibration software.

Optical densities (OD) of bacteria cultures (100 µL) at 600 nm were measured in 96 well plates on an Epoch2 microplate reader (Biotek). Time course experiments were done by measuring the OD at 600 nm using 100 µL bacteria suspension in 96 well plates with a cover at 28° C. and with continuous orbital shaking at 237 cpm (cycles per minute).

$^1$H NMR spectra were recorded on a Varian Mercury 400 MHz or Varian System 500 MHz spectrometer in deuterated chloroform (CDCl$_3$) or DMSO (d$_6$-DMSO). The number of scans was 32-64 and the D1 was 1 second for small compounds and 10 seconds for polymers.

The plasma cleaner was a PDC-001-HGP instrument (Harrick Plasma).

The pH of solutions was measured with an Oakton pH 700 instrument.

Materials

N-hydroxy succinimide (NHS), dicyclohexyl carbodiimide (DCC) and poly(ethylene glycol) (PEG)-diamine (MW 3400), deuterated chloroform (CDCl$_3$), phosphorpentoxide (P$_4$O$_{10}$), sodium phosphate dibasic (NaH$_2$PO$_4$), Alconox detergent, sodium hydroxide (NaOH), triethylamine (Et$_3$N), trichloro(1H,1H,2H,2H-perfluorooctyl)silane, 1 M HCl (aq) and anhydrous toluene were purchased from Aldrich. Four arm PEG-thiol (MW 10000) was purchased from Sunbright (Japan). Dimethylformamide (DMF), ethanol (EtOH), dichloromethane (CH$_2$Cl$_2$), ethyl acetate (EtOAc), diethyl ether (Et$_2$O), sodium hydrogen sulfate (NaHSO$_4$), anhydrous magnesium sulfate (MgSO$_4$), and isopropanol was purchased from Fisher. Fluorescein maleimide was purchased from Cayman. All chemicals were used as received unless stated otherwise. CH$_2$Cl$_2$ and Et$_3$N were dried over 4 Å molecular sieves.

Tryptone soy agar, yeast extract, kanamycin, isopropylthiogalactoside (IPTG), triphenyltetrazolium chloride (TTC), Tween20, and sodium chloride (NaCl) were purchased from Sigma-Aldrich. *A. tumefaciens* C58 pSRKKm-mCherry was prepared using established electroporation methods. This plasmid carries the gene encoding the fluorescent protein mCherry under control of the lac promoter allowing for IPTG induction of mCherry expression.

Synthesis of the Photodegradable Poly(Ethylene Glycol) PEG Diacrylate

Figure 16:
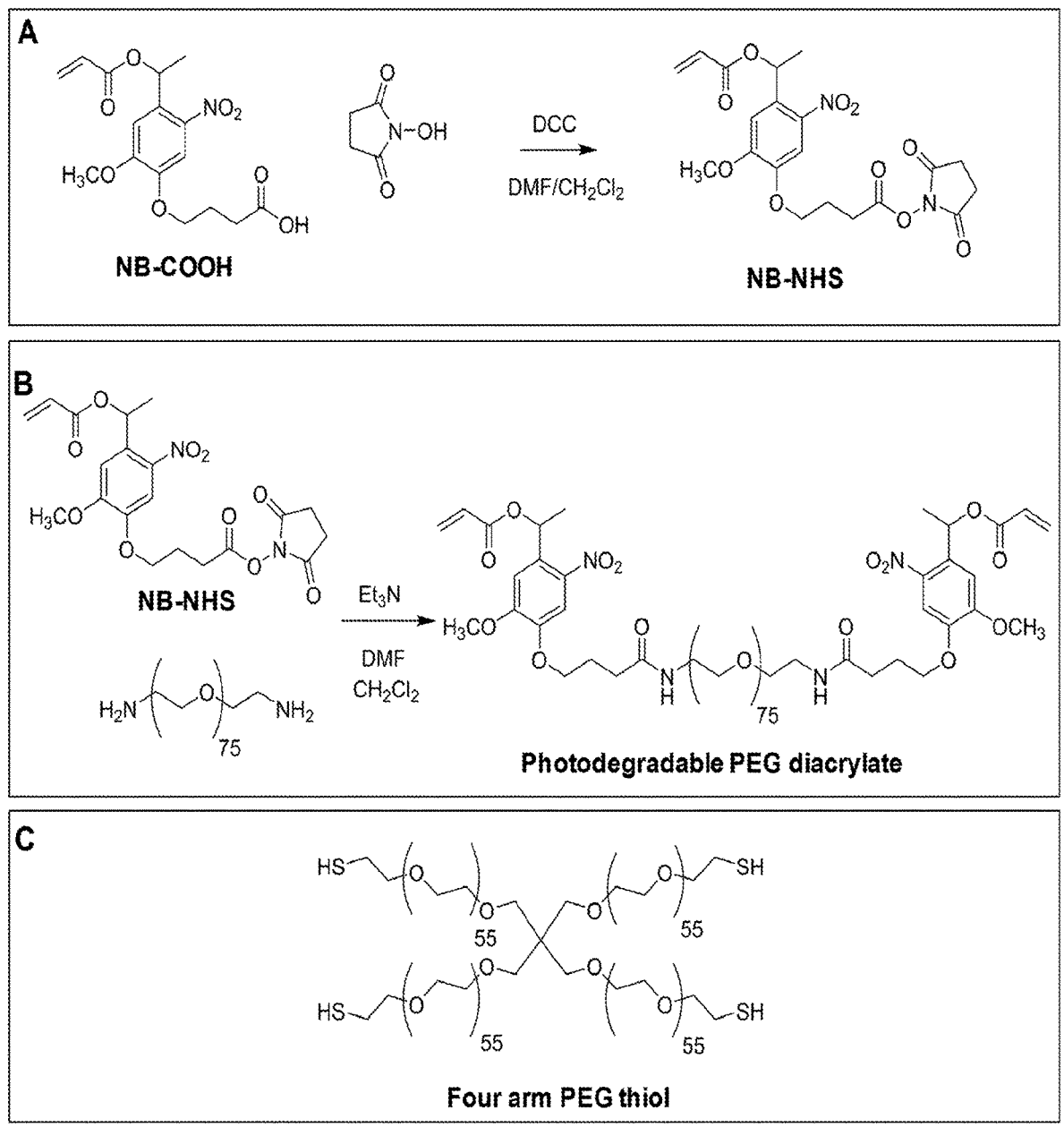
FIG. 16 shows reaction schemes for (A) synthesis of NB-NHS; (B) synthesis of photodegradable PEG diacrylate; and (C) chemical structure of the four arm PEG thiol used in the working examples.

The polymer was prepared in in a different way by reacting PEG-diamine with the N-hydroxysuccinimide ester of the nitrobenzyl carboxylic acid as outlined in FIG. 16.

NB-NHS. NB-COOH was first prepared in five steps starting from acetovanillone. The $^1$H NMR chemical shifts in CDCl$_3$ or d$_6$-DMSO for all intermediates were consistent with reported $^1$H NMR chemical shifts.

251.6 mg (0.71 mmol) of NB-COOH and 82.0 mg (0.71 mmol) of NHS were dissolved in a mixture of 2 mL DMF and 4 mL CH$_2$Cl$_2$. The solution was cooled at 0° C. for 25 minutes before a solution of 146.9 mg (0.71) mmol of DCC in 2 mL CH$_2$Cl$_2$ was added. The mixture was stirred for 19 hours. The suspension was concentrated in a flow of nitrogen and filtered through a plug of glass wool inside a glass Pasteur pipette. The residue was washed with 2 mL EtOAc and the filtrate diluted to 25 mL with the same solvent. The yellow solution was washed with water (3×25 mL), dried over MgSO$_4$ and concentrated in a flow of nitrogen. The solid was dried under reduced pressure to yield NB-NHS as a yellow solid in quantitative yield. $^1$H NMR (CDCl$_3$) δ=7.60 (s, 1H, CH$_{aromat}$), 7.01 (s, 1H, CH$_{aromat}$), 6.54 (m, 1H, CH), 6.43 (d, 1H, CH=CH$_{trans}$), 6.17 (dd, 1H, CH=CH$_2$), 5.87 (d, 1H, CH=CH$_{cis}$), 4.16 (t, 2H, CH$_2$O), 3.91 (s, 3H, OCH$_3$), 2.88 (t, 2H, CH$_2$CO), 2.84 (s, 4H, COCH$_2$CH$_2$CO), 2.29 (m, 2H, CH$_2$CH$_2$CH$_2$), 1.66 (d, 2H, CH$_3$CH).

NB-NHS and PEG-diamine were dried under reduced pressure in the presence of P$_4$O$_{10}$ at 40° C. to constant weight. 317.8 mg (0.71 mol, 4.2 eq relative to amine) NB-NHS was dissolved in 2 mL CH$_2$Cl$_2$ and to the slightly hazy solution was added over the course of 5 minutes a solution of 290 mg (0.085 mmol, 0.17 mmol amine groups) PEG-diamine and 29.7 µL (0.21 mmol) Et$_3$N in 5 mL CH$_2$Cl$_2$. The mixture became clear and was stirred in the dark at room temperature. After 23 hours the solution was concentrated in a flow of nitrogen and the residue suspended in 2 mL CH$_2$Cl$_2$. The mixture was filtered and the residue washed with CH$_2$Cl$_2$ (2×2 mL). The filtrate was diluted with 100 mL Et$_2$O to precipitate the polymer that was recovered by filtration through a glass filter. The residue was dissolved in 25 mL 1 M NaHSO$_4$ (aq) and filtered (0.22 µm). The clear solution was extracted with CH$_2$Cl$_2$ (3×25 mL), dried over MgSO$_4$ and concentrated in a flow to a volume of 6 mL. This solution was diluted with 100 mL Et$_2$O to precipitate the polymer. The polymer was recovered by filtration, dissolved in 8 mL CH$_2$Cl$_2$ and diluted with 100 mL Et$_2$O. The precipitate was filtered, dried under reduced pressure to yield 267.1 mg of a faint yellow solid. $^1$H NMR (CDCl$_3$) δ=7.58 (s, CH$_{aromat}$), 6.99 (s, 1H, CH$_{aromat}$), 6.51 (m, CH+NH), 6.42 (d, CH=CH$_{trans}$), 6.15 (dd, CH=CH$_2$), 5.86 (d, CH=CH$_{cis}$), 4.10 (t, CH$_2$O), 3.92 (s, OCH$_3$), 4.18-3.26 (CH$_2$CH$_2$O), 2.38 (t, CH$_2$NH), 2.16 (m, CH$_2$CH$_2$CH$_2$), 1.64 (d, CH$_3$CH). The degree of functionalization for a MW=3400 was 80% by comparing the integral ratios of the aromatic and CH$_2$CH$_2$ PEG protons. This degree of functionalization was considered when preparing the aqueous stock solutions.

Microwell Fabrication

Figure 17:
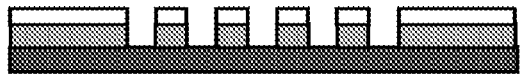
FIG. 17 is a schematic illustration of microwell fabrication, seeding, entrapment with the hydrogel membrane, and incubation procedure for monitoring the growth of the focal species.
Figure 17:
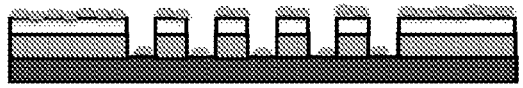
Figure 17:
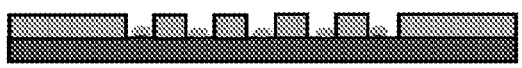
Figure 17:
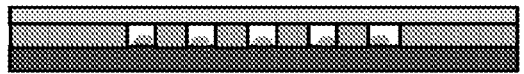
Figure 17:
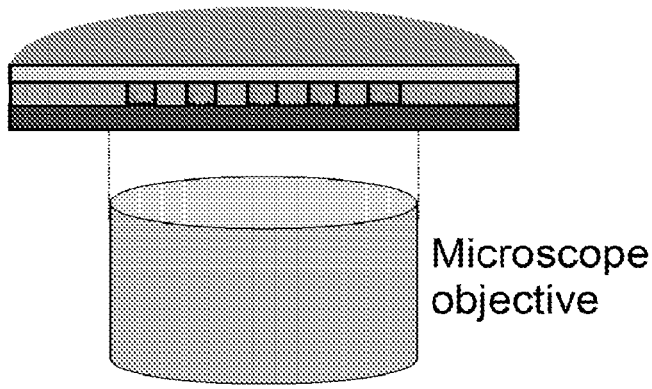

Microwell arrays were fabricated to contain a parylene liftoff mask to allocate cells in microwells while eliminating background cells, according to the procedures outlined in Hansen et al. *Stochastic assembly of bacteria in microwell arrays reveals the importance of confinement in community development.* PLoS One 2016, 11, e0155080, and illustrated in FIG. 17. Arrays were designed to contain wells with diameters ranging from 8 to 200 µm at different pitches.

Bacteria Culture

LB medium was supplemented with 150 µg/mL kanamycin and 0.5 mM IPTG and prepared fresh for each experiment from frozen stocks stored at −20° C. Under laminar flow a frozen 25% glycerol stock of *A. tumefaciens* was inoculated in 2 mL LB medium in round bottom borosilicate glass tubes (13 mm×100 mm, 10 mL) Globe Scientific. The culture tubes were closed with Bacti-caps (Clark Scientific) having openings to provide oxygen at atmospheric conditions inside the tube. Cultures were grown at 28° C. for 22 hours by shaking at 200 rpm. After spinning down at 2000 g for 10 minutes the bacteria pellet was suspended in medium and diluted 1:250 in fresh medium (culture volume 2 mL). After 11 hours at 28° C. and 200 rpm the bacteria reached mid-log phase and the culture had a typical OD of 0.2 (100 μL). The bacteria were spun down at 2000 g for 10 minutes and re-suspended in 100 μL of fresh LB medium at the desired OD.

Hydrogel Fabrication

Crosslinking Buffers

Phosphate buffered saline LB pH8 was prepared by adding $NaH_2PO_4$ to LB and adjusting the pH of the solution with 5 M NaOH (aq). The final phosphate concentration was 100 mM. This solution was sterile filtered, lyophilized and dissolved in half the volume of ultrapure water to make the 2× LB phosphate buffer solution used for hydrogel fabrication.

Membrane Precursor Solutions

Solutions of four arm-PEG thiol and photodegradable PEG diacrylate in ultrapure water were sterile filtered, aliquoted, lyophilized and stored at −20° C. for long-term use. Working solutions were prepared by dissolving aliquots in water to give four arm PEG thiol and photodegradable PEG diacrylate solutions with concentrations of 20 mM and 49 mM, respectively, and stored at −20° C. until use. Because of the high PEG concentration, the amount of water added to make the solutions was corrected by subtracting the volume of PEG calculated from the amount dissolved assuming a PEG density of 1 g/mL.

Perfluoroalkylated Glass Slides

Five glass slides 25×75×1 mm (Fisher Scientific) were washed with 20 mL of a 2% w/v Alconox solution for 20 minutes with sonication inside a polypropylene slide mailer. Slides were then washed with ultrapure water (3×20 mL) and finally sonicated in water (20 mL) for 20 minutes. Slides were blown dry with nitrogen and both sides plasma treated for 2 minutes in air at 800 mTorr with the RF power set to high output (45 W). The slides were placed inside a slide mailer and 20 mL of 0.5% v/v of trichloro(1H,1H,2H,2H-perfluorooctyl)silane in toluene was added. After 3 hours at room temperature the slides were washed with toluene (3×20 mL) and EtOH (3×20 ml) and dried by blowing nitrogen. For long term storage the slides were kept in 70% isopropanol. Slides prepared in this way were easier to separate after membrane preparation compared to slides prepared by chemical vapor deposition under reduced pressure inside a vacuum desiccator.

Spacers to Control Membrane Thickness

Initial thickness of the membrane was controlled in the range 38 to 102 μm using steel thickness feeler gage poc-kit assortment blades (Precision Brand).

Encapsulation of *A. Tumefaciens* Inside the Hydrogel

Bacteria in the mid-log phase were diluted to an OD of 0.2 (100 μL). The cell suspensions were spun down in a 500 μL Eppendorf tube and re-suspended in 2× LB phosphate buffer after supernatant removal. 5.6 μL of the photodegradable PEG diacrylate was added and the suspension carefully mixed with the pipette, then 6.9 μL of the four arm PEG thiol solution was added. After careful mixing the mixture was pipetted (e.g. 4×6 μL) onto a glass slide having 102 μm spacers on opposite sides (FIG. 4). A second glass slide was placed on top and left for 25 minutes at room temperature for thiol-acrylate crosslinking and subsequent hydrogel formation. After carefully separating the slides, membranes were washed with LB (5×1 mL) to remove non-encapsulated bacteria. The membranes were then placed inside a 24 well plate in 2 mL LB and cultured in the incubator at 28° C. without shaking.

Cell Viability Assay.

TTC was dissolved in LB medium at 5 mg/mL and diluted 10-fold into LB medium containing the hydrogel.

Membrane Fabrication on Microwells Directly

Figure 2D:
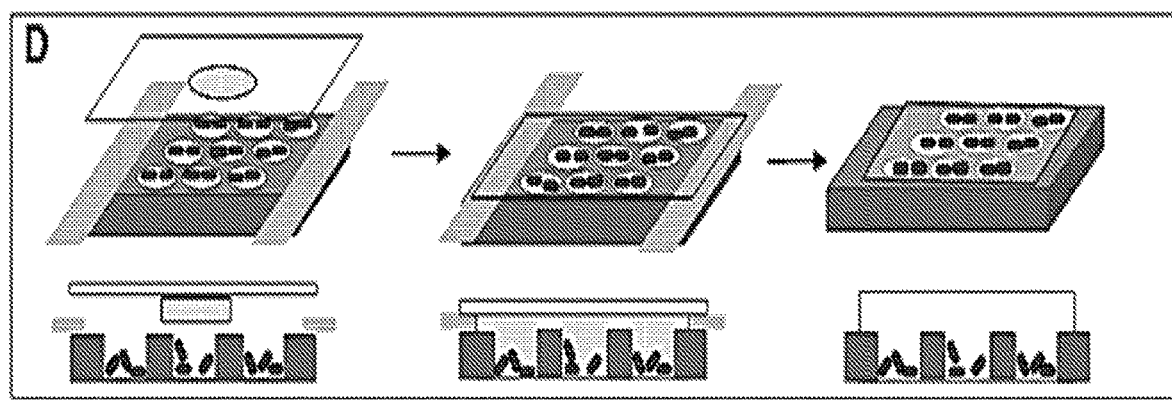
FIG. 2D illustrates an embodiment for using the photodegradable hydrogel to seal seeded cells into microwells using spacers, in which a glass slide with a mixture of the precursor is placed on top of the seeded microwell with spacers in between. The membrane precursor solution mixes with the medium inside the wells and crosslinks to form the membrane. After removing the glass slide the membrane swells (yellow) when the microwell placed in the culture medium.
Figure 18:
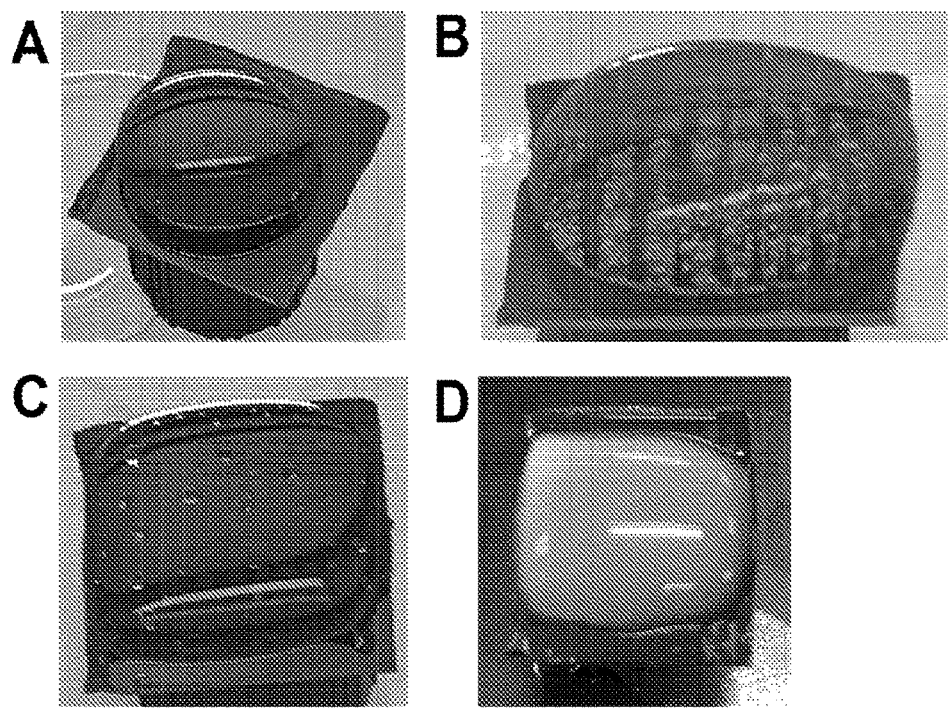
FIG. 18 are photographs of the approach for seeding bacteria into the microwells. (A) Prior to cell seeding the hydrophobic parylene-coated microwell is layered with LB medium and (B) put under reduced pressure to remove air from the microwells. (C) Filling the microwells with LB increases wettability of the parylene surface. (D) After removing the LB medium the bacteria suspension is added to seed the microwells.
Figure 19:
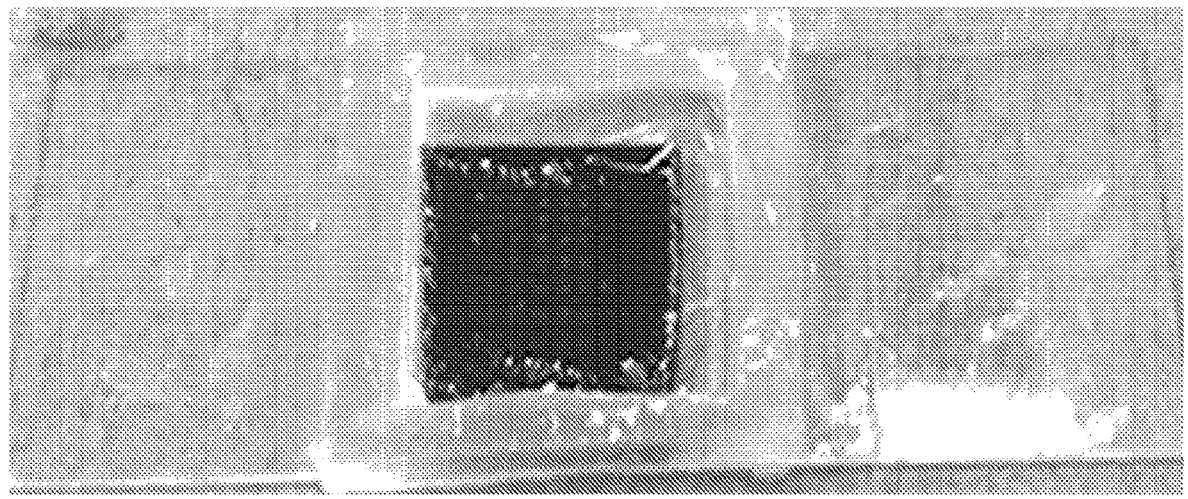
FIG. 19 is a photograph of a prototype slide used for culturing and the photodegradation experiments, including a PDMS rectangle glued onto a glass slide for holding the microwells. By adjusting the height of the border, the culture volume can be controlled (1-2 mL).

The microwell array was layered with 600 μL medium and placed inside a desiccator. A vacuum was applied for 30 minutes to replace air trapped inside the wells with LB medium (FIG. 18). For experiments without bacteria the surface was blotted at the sides with Kimwipes tissue paper and the parylene carefully removed using Scotch tape. For experiments with *A. tumefaciens*, the wells were inoculated with 600 μL of a bacteria suspension (OD=0.2). After 1 hour the bacteria suspension was removed with a pipette and the array carefully blotted with a Kimwipe before removing the parylene with Scotch tape. For microarrays without parylene coating, bacteria could also be removed with a PDMS slab after seeding. Immediately after cell seeding, 12.5 μL of 2× LB phosphate buffer was mixed with 5.6 μL of the photodegradable PEG diacrylate and 6.9 μL of the four arm PEG thiol, then 15 μL of the mixture pipetted onto a glass slide. The glass slide was inverted and placed on top of the microwell array having two 38 μm spacers on opposite sides (FIG. 2D) and incubated at room temperature for 25 minutes for hydrogel formation. After careful separation of the glass slide from the microwell array, the membrane-covered microwell array was placed inside a rectangular well made of polydimethylsiloxane on a glass slide containing 1-2 mL of LB medium (FIG. 19) and kept inside the incubator at 28° C. without shaking. This setup prevented drying up of the membrane and enabled easy handling of the microwell array on the microscope stage.

Membrane Degradation with the Polygon400

The microarray with membrane was kept in LB medium during the experiments in order to prevent membrane dehydration and to dissipate local heating due to the LED light. In addition, immersion in the medium allowed PEG products cleaved from the membrane to solubilize and diffuse away from the wells during irradiation. The Polygon400 tool allows for exposure of a user-defined pattern light in any shape within the working area of the objective, as well as control of light intensity and irradiation time. Light patterning experiments were done using 10× and 20× objectives, corresponding to (maximum) rectangular working areas of 330 μm×590 μm and 165 μm×295 μm, respectively.

Fluorescent-Labeling of the Membrane

After light exposure, membranes were visualized by fluorescence microscopy by coupling pendant thiol groups with fluorescein maleimide: 20 μL of a 10 mM stock solution of fluorescein maleimide in DMF was added to the microwell array in 1 mL of LB. This reaction occurs in the pH range 6.5-7.4 and was therefore done directly in LB (pH 6.7). Labeling was typically done for 2 hours or overnight. Before image collection the membrane was washed with LB (3×1 mL) to remove unreacted fluorophore.

Fixing Bacteria Inside the Hydrogel and Microwells

The bacteria were fixed in 2.5% glutaraldehyde and 2.5% formaldehyde overnight in LB and washed with LB (3×1 mL) before the confocal microscope measurements.

Retrieval of Live Bacteria from Membrane-Covered Microwell Arrays

*A. tumefaciens* was seeded at OD=0.2 (100 μL), washed with LB medium (2×5 mL), placed inside a polystyrene Petri dish and cultured for 24 hours in 5 mL LB medium at 28° C. without shaking. The array was washed (2×5 mL) with extraction medium (0.05% Tween20 in LB) to remove any bacteria that could be present outside the membrane, and placed inside the sample holder. The array was again washed in the sample holder with extraction medium (4×2 mL) using a pipette. The washings were spun down at 2000 g for 10 minutes and the supernatant carefully removed leaving 1 mL inside the culture tube. This sample served as the negative control. The microarray was immersed in 1 mL extraction medium and a total of 72 wells were opened in four different runs. After the experiment, another 1 mL of extraction medium was added and the wells washed by pipette. After transferring the washing to a culture tube the microwell array was washed with additional extraction medium (3×2 mL). The washings were combined and spun down at 2000 g for 10 minutes and the supernatant carefully removed leaving 1 mL inside the culture tube. After suspending with the pipette, a volume of 100 µL of retrieved bacteria and 100 µL of the negative control were placed inside the well plate and the OD at 600 nm was measured as function of time inside a plate reader. The remaining (0.9 mL) solutions were placed inside an incubator at 28° C. and shaken at 200 rpm.

The invention claimed is:

1. A method of selective retrieval of microbial targets from cell culture, comprising:
providing a sealed cell culture device, said device comprising:
a substrate having a top surface and a plurality of microwells formed therein, wherein each microwell is defined by a respective opening in the top surface, a bottom surface spaced from the top surface, and an interior sidewall extending between the opening and bottom surface, wherein one or more of said microwells comprises one or more microbes distributed therein; and
a crosslinked hydrogel membrane adjacent said top surface, wherein said membrane seals the respective opening of one or more of said microwells such that said microbes are confined to their respective microwells;
exposing said crosslinked hydrogel membrane to a pattern of light to yield exposed and unexposed areas of said crosslinked hydrogel membrane, wherein said exposed areas are degraded over one or more microwells of interest such that the seal over said one or more microwells of interest is broken to yield unsealed microwells, wherein said unexposed areas over one or more adjacent microwells remain sealed; and
selectively retrieving microbial targets only from said one or more unsealed microwells.

2. The method of claim 1, wherein said providing a sealed cell culture device comprises:
culturing a plurality of microbes in respective microwells in said cell culture device; and
forming said crosslinked hydrogel membrane adjacent said top surface to thereby seal said microbes in said respective microwells.

3. The method of claim 2, further comprising applying cell culture media adjacent said crosslinked hydrogel membrane.

4. The method of claim 2, wherein said forming said crosslinked hydrogel membrane comprises applying a hydrogel precursor solution to said substrate, such that said precursor solution is distributed across said top surface and flows into at least a portion of said microwells before crosslinking.

5. The method of claim 4, wherein said hydrogel precursor solution comprises a plurality of crosslinkable hydrophilic polymers wherein at least one polymer has a photolabile protecting group.

6. The method of claim 5, wherein said hydrogel precursor solution comprises a mixture of polyethylene glycol diacrylate monomer functionalized with a photolabile protecting group, and a polyethylene glycol tetrathiol crosslinker dispersed in phosphate buffered saline.

7. The method of claim 5, wherein said photolabile protecting group is selected from the group consisting of nitrobenzyl compounds and derivatives thereof, nitrophenethyl compounds and derivatives thereof, o-nitrobenzyloxycarbonyl, carbonyl-based protecting groups, benzyl-based protecting group, coumarin derivatives, p-methoxyphenacyl groups and derivatives, 3-nitro-2-naphthalenemethanol, and Type I photoinitiators.

8. The method of claim 2, wherein said forming said crosslinked hydrogel membrane comprises applying a pre-formed layer or film of crosslinked hydrogel adjacent said top surface.

9. The method of claim 2, wherein said crosslinked hydrogel membrane has an initial thickness and wherein said crosslinked hydrogel membrane swells to an increased thickness upon contact with cell culture media in said microwells.

10. The method of claim 1, wherein said cell culture device is a microfluidics substrate, wherein said microwell is a microchannel.

11. The method of claim 1, wherein said microbes are selected from the group consisting of bacteria, fungi, viruses, and microbial parasites.

12. The method of claim 1, wherein two or more microbes are combined in each of said microwells.

13. The method of claim 1, wherein said pattern is generated by direct patterning of a delimited light pattern directed onto the crosslinked hydrogel membrane without a mask.

14. The method of claim 1, wherein said pattern is generated by exposing said crosslinked hydrogel membrane though a mask having open areas and closed areas.

15. The method of claim 1, wherein said pattern of light comprises perimeter-only illumination of the crosslinked hydrogel membrane above each microwell of interest corresponding to the perimeter of each microwell opening exposed.

16. The method of claim 1, wherein said substrate is substantially transparent.

17. The method of claim 1, wherein said crosslinked hydrogel membrane is substantially transparent.

18. The method of claim 1, wherein said pattern of light comprises a channel from one or more unsealed microwells to guide motile microbes out of said one or more unsealed microwells.

19. The method of claim 1, further comprising detecting a positive or antagonistic interaction between microbes in said microwell of interest before exposing said crosslinked hydrogel membrane.

20. The method of claim 19, wherein at least one of said microbes expresses a detectable signal, said method comprising selectively retrieving said microbes from said microwell of interest after said exposing and sequencing said microbes for identification.

* * * * *